US011708577B2

(12) United States Patent
Fillatti et al.

(10) Patent No.: US 11,708,577 B2
(45) Date of Patent: *Jul. 25, 2023

(54) MODIFIED GENE SILENCING

(71) Applicant: Monsanto Technology LLC, St. Louis, MO (US)

(72) Inventors: Joanne Fillatti, Davis, CA (US); Jean C. Goley, Chesterfield, MO (US); Gregory R. Heck, Crystal Lake Park, MO (US); Tichafa R. I. Munyikwa, Ballwin, MO (US); Ty T. Vaughn, Clayton, MO (US); Toni Voelker, Davis, CA (US)

(73) Assignee: Monsanto Technology LLC, St. Louis, MO (US)

( * ) Notice: Subject to any disclaimer, the term of this patent is extended or adjusted under 35 U.S.C. 154(b) by 185 days.

This patent is subject to a terminal disclaimer.

(21) Appl. No.: 16/701,782

(22) Filed: Dec. 3, 2019

(65) Prior Publication Data
US 2020/0109410 A1     Apr. 9, 2020

Related U.S. Application Data

(60) Continuation of application No. 15/702,384, filed on Sep. 12, 2017, now abandoned, which is a continuation of application No. 14/322,393, filed on Jul. 2, 2014, now Pat. No. 9,765,351, which is a continuation of application No. 12/749,553, filed on Mar. 30, 2010, now abandoned, which is a division of application No. 11/674,207, filed on Feb. 13, 2007, now abandoned.

(60) Provisional application No. 60/772,614, filed on Feb. 13, 2006.

(51) Int. Cl.
C12N 15/82 (2006.01)

(52) U.S. Cl.
CPC ..... *C12N 15/8216* (2013.01); *C12N 15/8218* (2013.01); *C12N 15/8247* (2013.01)

(58) Field of Classification Search
None
See application file for complete search history.

(56) References Cited

U.S. PATENT DOCUMENTS

| | | |
|---|---|---|
| 4,557,734 A | 12/1985 | Schwab et al. |
| 5,004,863 A | 4/1991 | Umbeck |
| 5,015,580 A | 5/1991 | Christou et al. |
| 5,107,065 A | 4/1992 | Shewmaker et al. |
| 5,159,135 A | 10/1992 | Umbeck |
| 5,190,931 A | 3/1993 | Inouye |
| 5,208,149 A | 5/1993 | Inouye |
| 5,272,065 A | 12/1993 | Inouye et al. |
| 5,283,184 A | 2/1994 | Jorgensen et al. |
| 5,416,011 A | 5/1995 | Hinchee et al. |
| 5,453,566 A | 9/1995 | Shewmaker et al. |
| 5,454,842 A | 10/1995 | Poirier et al. |
| 5,463,174 A | 10/1995 | Moloney et al. |
| 5,475,099 A | 12/1995 | Knauf et al. |
| 5,500,361 A | 3/1996 | Kinney |
| 5,516,980 A | 5/1996 | Fehr et al. |
| 5,518,908 A | 5/1996 | Corbin et al. |
| 5,538,880 A | 7/1996 | Lundquist et al. |
| 5,550,318 A | 8/1996 | Adams et al. |
| 5,569,834 A | 10/1996 | Hinchee et al. |
| 5,591,616 A | 1/1997 | Hiei et al. |
| 5,593,874 A | 1/1997 | Brown et al. |
| 5,627,061 A | 5/1997 | Barry et al. |
| 5,633,435 A | 5/1997 | Barry et al. |
| 5,714,670 A | 2/1998 | Fehr et al. |
| 5,723,595 A | 3/1998 | Thompson et al. |
| 5,723,761 A | 3/1998 | Voelker et al. |
| 5,750,845 A | 5/1998 | Fehr et al. |
| 5,750,848 A | 5/1998 | Krüger et al. |
| 5,759,829 A | 6/1998 | Shewmaker et al. |
| 5,763,245 A | 6/1998 | Greenplate et al. |
| 5,780,708 A | 7/1998 | Lundquist et al. |
| 5,824,877 A | 10/1998 | Hinchee et al. |
| 5,850,026 A | 12/1998 | Debonte et al. |
| 5,859,347 A | 1/1999 | Brown et al. |
| 5,888,947 A | 3/1999 | Lambert et al. |
| 5,891,203 A | 4/1999 | Ball et al. |

(Continued)

FOREIGN PATENT DOCUMENTS

| | | |
|---|---|---|
| AU | 760041 B2 | 5/2003 |
| BR | 0308614 A | 2/2005 |

(Continued)

OTHER PUBLICATIONS

Xiangri 1998 (Soybean Science 17:4, p. 326-330) (Year: 1998).*
Allen et al., "microRNA-Directed Phasing during Trans-Acting siRNA Biogenesis in Plants," *Cell*, 121:207-221 (2005).
Alvarez et al., "Endogenous and Synthetic MicroRNAs Stimulate Simultaneous, Efficient, and Localized Regulation of Multiple Targets in Diverse Species," *The Plant Cell*, 18:1134-1151 (2006)
Bayer et al., "Programmable ligand-controlled riboregulators of eukaryotic gene expression," *Nature Biotechnol.*, 23:337-343 (2005).

(Continued)

*Primary Examiner* — Matthew R Keogh
(74) *Attorney, Agent, or Firm* — Morrison & Foerster LLP

(57) ABSTRACT

This invention relates to methods of controlling gene expression or gene suppression in eukaryotic cells. One aspect of this invention includes modifying the degree of silencing of a target gene by use of a modified suppression element. Another aspect includes providing a eukaryotic cell having a desired phenotype resulting from transcription in the eukaryotic cell of a modified suppression element. Also provided are transgenic eukaryotic cells, transgenic plant cells, plants, and seeds containing modified suppression elements, and useful derivatives of such transgenic plant cells, plants, or seeds, such as food or feed products.

18 Claims, 3 Drawing Sheets

(56) References Cited

U.S. PATENT DOCUMENTS

| | | |
|---|---|---|
| 5,955,329 A | 9/1999 | Yuan et al. |
| 5,955,650 A | 9/1999 | Hitz |
| 5,981,840 A | 11/1999 | Zhao et al. |
| 6,013,114 A | 1/2000 | Hille et al. |
| 6,022,577 A | 2/2000 | Chrysam et al. |
| 6,118,047 A | 9/2000 | Anderson et al. |
| 6,133,509 A | 10/2000 | Fehr et al. |
| 6,150,512 A | 11/2000 | Yuan |
| 6,153,812 A | 11/2000 | Fry et al. |
| 6,160,208 A | 12/2000 | Lundquist et al. |
| 6,194,636 B1 | 2/2001 | McEhoy et al. |
| 6,207,879 B1 | 3/2001 | McEhoy et al. |
| 6,232,526 B1 | 5/2001 | McEhoy et al. |
| 6,288,312 B1 | 9/2001 | Christou et al. |
| 6,331,664 B1 | 12/2001 | Rubin-Wilson et al. |
| 6,369,296 B1 | 4/2002 | Ratcliff et al. |
| 6,372,965 B1 | 4/2002 | Lightner et al. |
| 6,380,462 B1 | 4/2002 | Kridl |
| 6,384,301 B1 | 5/2002 | Martinell et al. |
| 6,399,861 B1 | 6/2002 | Anderson et al. |
| 6,403,865 B1 | 6/2002 | Koziel et al. |
| 6,426,446 B1 | 7/2002 | McEhoy et al. |
| 6,426,448 B1 | 7/2002 | Booth, Jr. et al. |
| 6,429,357 B1 | 8/2002 | McEhoy et al. |
| 6,433,252 B1 | 8/2002 | Kriz et al. |
| 6,437,217 B1 | 8/2002 | McEhoy et al. |
| 6,444,876 B1 | 9/2002 | Lassner et al. |
| 6,506,559 B1 | 1/2003 | Fire et al. |
| 6,573,099 B2 | 6/2003 | Graham |
| 6,583,338 B2 | 6/2003 | McEhoy et al. |
| 6,759,575 B2 | 7/2004 | Michiels et al. |
| 6,822,141 B2 | 11/2004 | Lardizabal et al. |
| 6,872,872 B1 | 3/2005 | Lightner et al. |
| 6,949,698 B2 | 9/2005 | Booth, Jr. et al. |
| 7,067,722 B2 | 6/2006 | Fillatti |
| 7,166,771 B2 | 1/2007 | Eenennaam et al. |
| 7,566,813 B2 | 7/2009 | Voelker |
| 7,601,888 B2 | 10/2009 | Fillatti et al. |
| 8,946,510 B2 | 2/2015 | Baum et al. |
| 2002/0034814 A1 | 3/2002 | Atabekov et al. |
| 2002/0133852 A1 | 9/2002 | Hauge et al. |
| 2003/0005491 A1 | 1/2003 | Hauge et al. |
| 2003/0049612 A1 | 3/2003 | Echt et al. |
| 2003/0049835 A1 | 3/2003 | Helliwell et al. |
| 2003/0135882 A1 | 7/2003 | Metzlaff et al. |
| 2003/0167537 A1 | 9/2003 | Jiang |
| 2003/0172399 A1 | 9/2003 | Fillatti |
| 2004/0006792 A1 | 1/2004 | Fillatti et al. |
| 2004/0029283 A1* | 2/2004 | Fillatti .............. C12N 9/0083 435/468 |
| 2004/0098761 A1 | 5/2004 | Trick et al. |
| 2004/0107460 A1 | 6/2004 | Fillatti et al. |
| 2004/0126845 A1 | 7/2004 | Eenennaam et al. |
| 2004/0216189 A1 | 10/2004 | Houmard et al. |
| 2005/0005333 A1 | 1/2005 | Ruezinsky et al. |
| 2005/0034190 A9 | 2/2005 | Fillatti et al. |
| 2006/0080750 A1 | 4/2006 | Fillatti et al. |
| 2006/0200878 A1 | 9/2006 | Lutfiyya et al. |
| 2006/0206963 A1 | 9/2006 | Voelker et al. |
| 2007/0074305 A1 | 3/2007 | Eenennaam et al. |
| 2008/0222756 A1 | 9/2008 | Fillatti et al. |
| 2009/0119805 A1 | 5/2009 | Fillatti et al. |
| 2009/0151029 A1 | 6/2009 | Voelker et al. |
| 2009/0307803 A1 | 12/2009 | Baum et al. |
| 2014/0080755 A1 | 3/2014 | Heck et al. |

FOREIGN PATENT DOCUMENTS

| | | |
|---|---|---|
| EP | 0 959 133 A1 | 11/1999 |
| WO | WO 94/10189 A1 | 5/1994 |
| WO | WO 94/11516 A1 | 5/1994 |
| WO | WO 95/06128 A1 | 3/1995 |
| WO | WO 96/06936 A1 | 3/1996 |
| WO | WO 97/40698 A1 | 11/1997 |
| WO | WO 98/05770 A2 | 2/1998 |
| WO | WO 98/30083 A1 | 7/1998 |
| WO | WO 98/46776 A2 | 10/1998 |
| WO | WO 98/53083 A1 | 11/1998 |
| WO | WO 98/56239 A1 | 12/1998 |
| WO | WO 99/15682 A2 | 4/1999 |
| WO | WO 99/32619 A1 | 7/1999 |
| WO | WO 99/49029 A1 | 9/1999 |
| WO | WO 99/53050 A1 | 10/1999 |
| WO | WO 99/61631 A1 | 12/1999 |
| WO | WO 99/63096 A2 | 12/1999 |
| WO | WO 99/64579 A2 | 12/1999 |
| WO | WO 00/01713 A2 | 1/2000 |
| WO | WO 00/07432 A1 | 2/2000 |
| WO | WO 00/18880 A2 | 4/2000 |
| WO | WO 00/44895 A1 | 8/2000 |
| WO | WO 00/44914 A1 | 8/2000 |
| WO | WO 00/68374 A1 | 11/2000 |
| WO | WO 01/11061 A2 | 2/2001 |
| WO | WO 01/14538 A2 | 3/2001 |
| WO | WO 01/34822 A2 | 5/2001 |
| WO | WO 01/35726 A1 | 5/2001 |
| WO | WO 01/36598 A1 | 5/2001 |
| WO | WO 01/70949 A1 | 9/2001 |
| WO | WO 01/79499 A1 | 10/2001 |
| WO | WO 02/04581 A1 | 1/2002 |
| WO | WO 02/10365 A2 | 2/2002 |
| WO | WO 02/15675 A1 | 2/2002 |
| WO | WO 02/057471 A2 | 7/2002 |
| WO | WO 02/059336 A2 | 8/2002 |
| WO | WO 02/062129 A2 | 8/2002 |
| WO | WO 02/081711 A1 | 10/2002 |
| WO | WO 02/088301 A2 | 11/2002 |
| WO | WO 03/080802 A2 | 10/2003 |
| WO | WO 2004/000871 A2 | 12/2003 |
| WO | WO 2004/001000 A2 | 12/2003 |
| WO | WO 2004/001001 A2 | 12/2003 |
| WO | 2004002871 A1 | 1/2004 |
| WO | WO 2005/007829 A2 | 1/2005 |
| WO | WO 2005/030982 A2 | 4/2005 |
| WO | WO 2005/079389 A2 | 9/2005 |
| WO | WO 2007/095243 A2 | 8/2007 |
| WO | WO 2011/005998 A1 | 1/2011 |

OTHER PUBLICATIONS

Becker et al., "Fertile transgenic wheat from microprojectile bombardment of scutellar tissue," *The Plant Journal*, 5:299-307 (1994).

Belfort et al., "Prokaryotic Introns and Inteins: a Panoply of Form and Function," *J. Bacteriol.*, 177:3897-3903 (1995).

Bennett et al., "Inhibition of Vascular Smooth Muscle Cell Proliferation in vitro and in vivo by C-myc Antisense Oligodeoxynucleotides," *J. Clin. Invest.*, 93:820-828 (1994).

Bosher et al., "RNA Interference can Target Pre-mRNA: Consequences for Gene Expression in a *Caenorhabditis elegans* Operon," *Genetics*, 153:1245-1256 (1999).

Bouchon et al., "Oil Distribution in Fried Potatoes Monitored by Infrared Microspectroscopy," *Journal of Food Science*, 66(7):918-923 (2001).

Burch-Smith et al., "Applications and advantages of virus-induced gene silencing for gene function studies in plants," *The Plant Journal*, 39:734-746 (2004).

Buhr et al., "Ribozyme Termination of RNA Transcripts Down-Regulate Seed Fatty Acid Genes in Transgenic Soybean," *The Plant Journal*, 30(2):155-163 (2002).

Byrum et al., "Alteration of the omega-3 fatty acid desaturase gene is associated with reduced linolenic acid in the A5 soybean genotype," *Theor. Appl. Genet.*, 94:356-359 (1997).

Bytebier et al., "T-DNA organization in tumor cultures and transgenic plants of the monocotyledon *Asparagus officinalis*," *Proc. Natl. Acad. Sci. U.S.A.*, 84:5345-5349 (1987).

Cartea et al., "Comparison of Sense and Antisense Methodologies for Modifying the Fatty Acid Composition of *Arabidopsis thaliana* Oilseed," *Plant Science*, 136:181-194 (1998).

Chapman et al., "Transgenic cotton plants with increased seed oleic acid content," *JAOCS*, 78:941-947 (2001).

(56) References Cited

OTHER PUBLICATIONS

Cheng et al., "Production of fertile transgenic peanut (*Arachis hypogaea* L.) plants using *Agrobacterium tumefaciens*," *Plant Cell Reports*, 15:653-657 (1996).
Chuang et al., "Specific and heritable genetic interference by double-stranded RNA in *Arabidopsis thaliana*," *PNAS*, 97:4985-4990 (2000).
Clancy et al., "Splicing of the Maize Sh1 First Intron is Essential for Enhancement of Gene Expression, and a T-Rich Motif Increases Expression without Affecting Splicing," *Plant Physiol.*, 130:918-929 (2002).
Clark-Walker et al., "Location of Transcriptional Control Signals and Transfer RNA Sequences in *Torulopsis glabrata* Mitochondrial DNA," *EMBO*, 4(2):465-473 (1985).
Cogoni et al., "Post-Transcriptional Gene Silencing Across Kingdoms," *Curr. Opin. Gen. & Devel.*, 10(6):638-643 (2000).
Colliver et al., "Differential modification of flavonoid and isoflavonoid biosynthesis with an antisense chalcone synthase construct in transgenic *Lotus corniculatus*," *Plant Mol. Biol.*, 35:509-522 (1997).
Crossway et al., "Integration of Foreign DNA Following Microinjection of Tobacco Mesophyll Protoplasts," *Mol. Gen. Genet.*, 202(2):179-185 (1986).
Database EM_GSS 'Online! EMBL Heidelberg, Germany; AC AL071390, May 29, 1999, Genoscope: "*Drosophila melanogaster* genome surface sequence TET3 end of BAC: BACR32M05," XP002163063, Abstract.
Database EMPLN 'Online! EMBL Heidelberg, Germany; AC/ID AC004705, May 21, 1998, Lin X et al.: "Sequence of chromosome 2 of the plant *Arabidopsis thaliana*," Abstract.
Database EM_GSS 'Online! EMBL Heidelberg, Germany; AC AL105179, Jul. 26, 1999, Genoscope: "*Drosophila melanogaster* genome survey sequence T7 end of BAC: BACN13A12" XP002163065, Abstract.
Database EM-NEW 'Online! EMBL Heidelberg, Germany; AC/ID AB022220, Jan. 15, 1999, Sato S. et al.: "*Arabidopsis thaliana* genomic DNA, chromosome 3, P1 clone: MLN21" XP002163066, Abstract.
Database EM_GSS 'Online! EMBL Heidelberg, Germany; AC AL069706, May 29, 1999, Genoscope: "*Drosophila melanogaster* genome survey sequence T7 end of BAC: BACR29B23" XP002163067, Abstract.
Database EM_GSS 'Online! EMBL Heidelberg, Germany; AC AL063932, May 29, 1999, Genoscope: "*Drosophila melanogaster* genome survey sequence TET3 end of BAC: BACR8010" XP002163068, Abstract.
Database EM_GSS 'Online! EMBL Heidelberg, Germany; AC AL08811, Jul. 26, 1999, Genoscope: "*Drosophila melanogaster* genome survey sequence SP6 end of BAC: BACN37D10" XP002163069, Abstract.
Database EM_NEW 'Online! EMBL Heidelberg, Germany; AC/ID AB026636, May 7, 1999, Sato S. et al.: "*Arabidopsis thaliana* genomic DNA, chromosome 3, TAC clone: K14A17," XP002163070, Abstract.
Database EMEST_PLN 'Online! EMBL Heidelberg, Germany; AC/ID AW297948, Feb. 8, 2000, Shoemaker R. et al.: "Public soybean EST project," XP002163071, Abstract.
Database EMPLN 'Online! EMBL Heidelberg, Germany; AC AL161581, Mar. 15, 2000, Weichselgartner M. et al.: "*Arabidopsis thaliana* chromosome 4, contig fragment No. 77," XP002163072, Abstract.
Daun et al., "Effect of Frost Damage on the Quality of Canola (*B. napus*)," *JAOCS*, 62(4):715-719 (1985).
Davidson et al., "Engineering regulatory RNAs," *TRENDS in Biotechnology*, 23(3):109-112 (2005).
De Framond, "MINI-Ti: A New Vector Strategy for Plant Genetic Engineering," *Nature Biotechnology*, 1:262-269 (1983).
DeLuca, "Molecular characterization of secondary metabolic pathways," *AgBiotech News and Information*, 5(6):225N-229N (1993).

Dehesh et al., "KAS IV: a 3-ketoacyl-ACP Synthase from *Cuphea* sp. is a Medium Chain Specific Condensing Enzyme," *The Plant Journal*, 15(3):383-390 (1998).
Dörmann et al., "Accumulation of Palmitate in *Arabidopsis* Mediated by the Acyl-Acyl Carrier Protein Thioesterase FATB1," *Plant Physiology*, 123:637-643 (2000).
Du et al., "A systematic analysis of the silencing effects of an active siRNA at all single-nucleotide mismatched target sites," *Nucleic Acids Research*, 33(5):1671-1677 (2005).
Dubois et al., "Fatty acid profiles of 80 vegetable oils with regard to their potential," *European Journal of Lipid Science and Technology*, 109:710-732 (2007).
Duffield et al., "U.S. Biodiesel Development: New Markets for Conventional and Genetically Modified Agricultural Products," *Economic Research Service USDA*, pp. 1-31 (1998).
Dunn et al., "Recent Advances in the Development of Alternative Diesel Fuel from Vegetable Oils and Animal Fats," *Recent Res. Devel. in Oil Chem.*, 1:31-56 (1997).
Erdmann et al., "The non-coding RNAs as riboregulators," *Nucleic Acids Res.*, 29:189-193 (2001).
Erhan et al., "Lubricant Basestocks from Vegetable Oils," *Industrial Crops and Products*, 11:277-282 (2000).
European Search Report dated May 4, 2011, in European Patent Application No. 10195208.
Extended European Search Report dated Mar. 11, 2015, in European Patent Application No. 14196149.0.
Fehr et al., "Breeding for fatty acid composition of soybean oil," VII World Soybean Research Conference, IV International Soybean Processing and Utilization Conference, III Congresso Mondial de Soja (Brazilian Soybean Congress) Proceedings, Feb. 29-Mar. 5, 2004, pp. 815-821.
Fire et al., "Potent and Specific Genetic Interference by Double-Stranded RNA in *Caenorhabditis elegans*," *Nature*, 391:806-811 (1998).
Gallie et al., "Identification of the motifs within the tobacco mosaic virus 5'-leader responsible for enhancing translation," *Nucleic Acids Res.*, 20:4631-4638 (1992).
Genbank Accession No. AJ459107 (2002).
Gendel, "Sequence Databases for Assessing the Potential Allergenicity of Proteins Used in Transgenic Foods," *Adv. Food Nutr. Res.*, 42:63-92 (1998).
Gryson et al., "Detection of DNA During the Refining of Soybean Oil," *JAOCS* 79(2):171-174 (2002).
Halpin et al., "Enabling Technologies for Manipulating Multiple Genes on Complex Pathways," *Plant Molecular Biology*, 47:295-310 (2001).
Hamada et al., "Modification of Fatty Acid Composition by Over- and Antisense-Expression of a Microsomal ω-3 Fatty Acid Desaturase Gene in Transgenic Tobacco," *Transgenic Research*, 5(2):115-121 (1996).
Hamilton et al., "A transgene with repeated DNA causes high frequency, post-transcriptional suppression of ACC-oxidase gene expression in tomato," (1998) *Plant J.*, 15(6):737-746 (1998).
Hannon, "RNA Interference," *Nature*, 418:244-251 (2002).
Helliwell et al., "High-throughput vectors for efficient gene silencing in plants," *Functional Plant Biology*, 29:1217-1225 (2002).
Hoekema et al., "A binary plant vector strategy based on separation of vir-and T-region of the *Agrobacterium tumefaciens* Ti-plasmid," *Nature*, 303:179-180 (1983).
International Preliminary Examination Report dated Dec. 6, 2001, in International Patent Application No. PCT/US00/22613.
International Preliminary Examination Report dated Jul. 27, 2004, in International Patent Application No. PCT/US03/19437.
International Search Report dated Nov. 13, 2003, in International Patent Application No. PCT/US03/08610.
International Search Report dated Jul. 12, 2005, in International Patent Application No. PCT/US04/31605.
International Search Report dated Apr. 9, 2004, in International Patent Application No. PCT/US03/19445.
International Search Report dated Jun. 21, 2004, in International Patent Application No. PCT/US03/019437.
International Search Report dated Apr. 26, 2001, in International Patent Application No. PCT/US00/22613.

(56) References Cited

OTHER PUBLICATIONS

International Search Report dated Oct. 1, 2007, in International Patent Application No. PCT/US07/003823.
Isaacs et al., "Engineered riboregulators enable post-transcriptional control of gene expression," *Nature Biotechnology*, 22(7):841-847 (2004).
Jaworski et al., "Industrial oils from transgenic plants," *Current Opinion in Plant Biology*, 6:178-184 (2003).
Griffiths-Jones et al., "Rfam: annotating non-coding RNAs in complete genomes," *Nucleic Acids Res.*, 33:121-124 (2005).
Kandimalla et al., "Design, biochemical, biophysical and biological properties of cooperative antisense oligonucleotides," *Nucleic Acids Research*, 23(17):3578-3584 (1995).
Kinney et al., "Designer oils: the high oleic acid soybean," *Genetic Modification* in the Food Industry, Chapter 10, pp. 193-213 (1998).
Kinney, "Plants as industrial chemical factories—new oils from genetically engineered soybeans," *Fett/Lipid*, 100(4-5):173-176 (1998).
Klahre et al., "High molecular weight RNAs and small interfering RNAs induce systemic posttranscriptional gene silencing in plants," *PNAS*, 99(18):11981-11986 (2002).
Kusaba, "RNA Interference in Crop Plants," *Current Opinion in Biotechnology*, 15:139-143 (2004).
Lang et al., "Preparation and characterization of bio-diesels from various bio-oils," *Bioresource Technology*, 80:53-62 (2001).
Liang et al., "Computational approaches to RNA structure prediction, analysis, and design," *Current Opinion in Structural Biology*, 21:306-318 (2011).
Lee et al., "Antisense Expression of the CK2 α-Subunit Gene in *Arabidopsis*. Effects on Light-Regulated Gene Expression and Plant Growth," *Plant Physiology*, 119:989-1000 (1999).
Lee et al., "MicroRNA maturation: stepwise processing and subcellular localization," *The EMBO Journal*, 21(17):4663-4670 (2002).
Levin et al., "Methods of Double-Stranded RNA-Mediated Gene Inactivation in *Arabidopsis* and Their Use to Define an Essential Gene in Methionine Biosynthesis," *Plant Mol. Biol.*, 44(6):759-775 (2000).
Lewin, "How Did Interrupted Genes Evolve?," *Genes*, 2nd Edition, pp. 333-337 (2009).
Lund et al., "Nuclear Export of MicroRNA Precursors," *Science*, 303:95-98 (2004).
Mallory et al., "MicroRNA control of Phabulosa in leaf development: importance of pairing to the microRNA 5' region," *EMBO Journal*, 23:3356-3364 (2004).
Mandal et al., "Adenine riboswitches and gene activation by disruption of a transcription terminator," *Nature Struct. Mol. Biol.*, 11:29-35 (2004).
Mandal et al., "Gene Regulation by Riboswitches," *Nature Reviews | Molecular Cell Biology*, 5:451-463 (2004).
Martin et al., "A comparison of Oleic Acid Metabolism n the Soybean (*Glycine max* [L.] Merr.) Genotypes Williams and A5, a mutant with decreased linoleic acid in the seed," *Plant Phys.*, 61:41-44 (1986).
Martinez-Rivas et al., "Oxygen-independent temperature regulation of the microsomal oleate desaturase (FAD2) activity in developing sunflower (*Helianthus annuus*) seeds," *Physiologia Plantarum*, 117:179-185 (2003).
Masoud et al., "Constitutive expression of an inducible ß-1,3-glucanase in alfalfa reduces disease severity caused by the oomycete pathogen *Phytophthora megasperma* f. sp *medicaginis*, but does not reduce diesease severity of chitin-containing fungi," *Transgenic Research*, 5:313-323 (1996).
Matzke et al., "Rna-Based Silencing Strategies in Plants," *Curr. Opin. Gen. & Devel.*, 11(2):221-227 (2001).
McCormick et al, "Effect of Humidity on Heavy-Duty Transient Emissions from Diesel and Natural Gas Engines at High Altitude," *Journal of the Air & Waste Management Association*, 47:784-791 (1997).
McElroy et al., "Isolation of an Efficient Actin Promoter for Use in Rice Transformation," *Plant Cell*, 2:163-171 (1990).
Meister et al., "Sequence-specific inhibition of microRNA- and siRNA-induced RNA silencing," *RNA*, 10(3):544-550 (2004).
Mensink et al., "Effect of Dietary Fatty Acids on Serum Lipids and Lipoproteins: A Meta-Analysis of 27 Trials," *Arteriosclerosis and Thrombosis*, 12(8):911-919 (1992).
Millar et al., "Plant and animal microRNAs: similarities and differences," *Funct. Integr. Genomics*, 5:129-135 (2005).
Montgomery et al., "RNA as a Target of Double-Stranded RNA-Mediated Genetic Interference in *Caenorhabditis elegans*," *Proc. Natl. Acad. Sci. USA*, 95(96):15502-15507 (1998).
Mroczka et al., "An Intron Sense Suppression Construct Targeting Soybean FAD2-1 Requires a Double-Stranded RNA-Producing Inverted Repeat T-DNA Insert," *Plant Physiology*, 153(2):882-891 (2010).
Napoli et al., "Introduction of a Chimeric Chalcone Synthase Gene into Petunia Results in Reversible Co-Suppression of Homologous Genes in trans," *The Plant Cell*, 2:279-289 (1990).
Neff et al., "Odor Significance of Undersirable Degradation Compounds in Heated Triolein and Trilinolein," *JAOCS*, 77(12):1303-1313 (2000).
Ngo et al., "Double-stranded RNA induces mRNA degradation in *Trypanosoma brucei*," *Proc. Natl. Acad. Sci. USA*, 95:14687-14692 (1998).
Okuley et al., "*Arabidopsis* FAD2 Gene Encodes the Enzyme that is Essential for Polyunsaturated Lipid Synthesis," *The Plant Cell*, 6:147-158 (1994).
Padgette et al., *Crop Sci.*, "Development, Identification, and Characterization of a Glyphosate-Tolerant Soybean Line," 35:1451-1461 (1995).
Parizotto et al., "In vivo investigation of the transcription, processing, endonucleolytic activity, and functional relevance of the spatial distribution of a plant miRNA," *Genes & Development*, 18:2237-2242 (2004).
Parrish et al., "Functional Anatomy of a dsRNA Trigger: Differential Requirement for the Two Trigger Strands in RNA Interference," *Molecular Cell*, 6:1077-7087 (2000).
Pauli et al., "Detection of DNA in soybean oil," *Z Lebensm Unters Forsch A*, 207:264-267 (1998).
Peele et al., "Silencing of a meristematic gene using geminivirus-derived vectors," *The Plant Journal*, 27(4):357-366 (2001).
Pokorný, "Flavor Chemistry of Deep Fat Frying in Oil," *Flavor Chemistry of Lipid Foods* (eds. Min & Smouse), Chapter 7, pp. 113-155, American Oil Chem. Soc., Champaign, IL (1989).
Qing, Thesis entitled "The Isolation and Characterisation of Fatty Acid Desaturase Genes in Cotton," University of Sydney, Australia, pp. ii-iv, 24 26, 121-123, 142, 167-168, 172-174, 179-181 (1998).
Reinhart et al., "MicroRNAs in plants," *Genes Dev.*, 16:1616-1626 (2002).
Reynolds et al., "Rational siRNA design for RNA interference," *Nature Biotechnol.*, 22 (3):326-330 (2004).
Sharma et al., "In Silico Identification and Comparative Genomics of Candidate Genes Involved in Biosynthesis and Accumulation of Seed Oil in Plants," *Comparative and Functional Genomics*, 2012:1-14 (2012).
Sharp, "RNAi and Double-Strand RNA," *Genes & Development*, 13:139-141 (1999).
Sharp, "RNA Interference—2001," *Genes & Development*, 15:485-490 (2001).
Singh et al., "Transgenic expression of a delta 12-epoxygenase gene in *Arabidopsis* seeds inhibits accumulation of linoleic acid," *Planta*, 212:872-879 (2001).
Singh et al., "Metabolic engineering of new fatty acids in plants," *Current Opinion in Plant Biology*, 8:197-203 (2005).
Sivaraman et al., "Development of high oleic and low linoleic acid transgenics in a zero erucic acid *Brassica juncea* L. (Indian mustard) line by antisense suppression of the fad2 gene," *Molecular Breeding*, 13:365-375 (2004).
Smith et al., "Total silencing by intron-spliced hairpin RNAs," *Nature*, 407:319-320 (2000).
Stam et al., "Post-transcriptional silencing of chalcone synthase in *Petunia* by inverted transgene repeats," *The Plant Journal*, 12(1):63-82 (1997).

(56) References Cited

OTHER PUBLICATIONS

Stam et al., "The Silence of Genes in Transgenic Plants," *Annals of Botany*, 79:3-12 (1997).
Stoutjeskijk et al., "hpRNA-Mediated Targeting of the *Arabidopsis* FAD 2 Gene Gives Highly Efficient and Stable Silencing," *Plant Physiology*, 129:1723-1731 (2002).
Sudarsan et al., "Metabolite-binding RNA domains are present in the genes of eukaryotes," *RNA*, 9:644-647 (2003).
Supplemental European Search Report completed dated Jul. 18, 2005, in European Patent Application No. 03711656.3.
Supplementary European Search Report dated Nov. 7, 2006, in European Patent Application No. 04 78 5109.
Supplementary European Search Report dated Jan. 8, 2007, in European Patent Application No. 03 76 1158.
Sweetlove et al., "Starch metabolism in tubers of transgenic potato (*Solanum tuberosum*) with increased ADPglucose pyrophosphorylase," *Biochemical Journal*, 320:493-498 (1996).
Thomas et al., "Size constraints for targeting post-transcriptional gene silencing and for RNA-directed methylation in *Nicotiana benthamiana* using a potato virus X vector," *The Plant Journal*, 25(4):417-25 (2001).
Timmons et al., "Relationships Among Dietary Roasted Soybeans, Milk Components, and Spontaneous Oxidized Flavor of Milk," *Journal of Diary Science*, 84(11):2440-2449 (2001).
Toborek et al., "Unsaturated Fatty Acids Selectively Induce an Inflammatory Environment in Human Endothelial Cells," *American Journal of Clinical Nutrition*, 75:119-125 (2002).
Toriyama et al., "Transgenic Rice Plants After Direct Gene Transfer Into Protoplasts," *Bio/Technology*, 6:1072-1074 (1988).
Van der Krol et al., "Flavonoid Genes in Petunia: Addition of a Limited Number of Gene Copies May Lead to a Suppression of Gene Expression," *The Plant Cell*, 2:291-299 (1990).
Vasil et al., "Increased Gene Expression by the First Intron of Maize Shrunken-1 Locus in Grass Species," *Plant Physiol.*, 91:1575-1579 (1989).
Vasil et al., "Herbicide Resistant Fertile Transgenic Wheat Plants Obtained by Microprojectile Bombardment of Regenerable Embryogenic Callus," *Bio/Technology*,10:667-674 (1992).
Voelker et al., "Variations in the Biosynthesis of Seed-Storage Lipids," *Annu Rev Plant Physiol Plant Mol Biol*, 52:335-361 (2001).
Wagner et al., "RNAi trigger fragment truncation attenuates soybean FAD2-1 transcript suppression and yields intermediate oil phenotypes," *Plant Biotechnology Journal*, 2010:1-8 (2010).
Wan et al., "Generation of Large Numbers of Independently Transformed Fertile Barley Plants," *Plant Physiol.*, 104:37-48 (1994).
Wang et al., "Characterization of cis-Acting Elements Regulating Transcription from the Promoter of a Constitutively Active Rice Actin Gene," *Mol. Cell Biol.*, 12:3399-3406 (1992).
Warner et al., "Effect of Oleic and Linoleic Acids on the Production of Deep-Fried Odor in Heated Triolein and Trilinolein," *Journal of Agricultural Food Chemical*, 49:899-905 (2001).
Waterhouse, P.M. et al., "Virus Resistance and Gene Silencing in Plants Can be Induced by Simultaneous Expression of Sense and Antisense RNA," *Proc. Natl. Acad. Sci. USA*, 95:13959-13964 (1998).
Wesley et al., "Construct Design for Efficient, Effective and High-Throughput Gene Silencing in Plants," *The Plant Journal*, 27(6):581-590 (2001).
Winkler et al., "Thiamine derivatives bindmessenger RNAs directly to regulate bacterial gene expression," *Nature*, 419:952-956 (2002).
Yamada et al., "Self-splicing group I introns in eukaryotic viruses," *Nucleic Acids Res.*, 22:2532-2537 (1994).
Yoshimatsu et al., "Control of Gene Expression by Artificial Introns in *Saccharomyces cerevisiae*," *Science*, 244:1346-1348 (1989).
Yu et al., "RNA interference by expression of short-interfering RNAs and hairpin RNAs in mammalian cells," *Proc. Natl. Acad. Sci.*, 99(9):6047-6052 (2002).
Zhang et al., "Transgenic rice plants produced by electroporation-mediated plasmid uptake into protoplasts," *Plant Cell Reports*, 7:379-384 (1988).
Cromwell, G. (2012). "Soybean Meal—An Exceptional Protein Source," located at <http://www.soymeal.org/ReviewPapers/SBMExceptionalProteinSource.pdf>, 15 pages.
GenBank Accession No. DQ861998.1, last updated Jul. 14, 2016, located at <https://www.ncbi.nlm.nih.gov/nuccore/DQ861998.1/>, last visited on Jan. 3, 2023, 2 pages.
GenBank Accession No. AJ271842.1, last updated Nov. 14, 2006, located at <https://www.ncbi.nlm.nih.gov/nuccore/AJ271842.1/>, last visited on Jan. 3, 2023, 1 page.
Liu, Q. et al. (Aug. 2002). "High-Stearic and High-Oleic Cottonseed Oils Produced by Hairpin RNA-Mediated Post Transcriptional Gene Silencing," Plant Physiology 129:1732-1743.
Newkirk, R. (2010). "Soybean Feed Industry Guide 1st Edition, 2010," located at <https://cigi.ca/wp-content/uploads/2011/12/2010-Soybean-Feed-Industry-Guide.pdf>, 48 pages.

\* cited by examiner

MODIFIED GENE SILENCING

CROSS-REFERENCE TO RELATED APPLICATIONS

This application is a continuation of U.S. patent application Ser. No. 15/702,384, filed Sep. 12, 2017, which is a continuation of U.S. patent application Ser. No. 14/322,393, filed Jul. 2, 2014 (now U.S. Pat. No. 9,765,351, issued: Sep. 19, 2017), which is a continuation of U.S. patent application Ser. No. 12/749,553, filed Mar. 30, 2010, which is a divisional of U.S. patent application Ser. No. 11/674,207, filed Feb. 13, 2007, which claims the benefit of U.S. Provisional Application No. 60/772,614, filed Feb. 13, 2016. All of which are incorporated by reference in their entireties herein.

FIELD OF THE INVENTION

Disclosed herein are methods of controlling gene expression in eukaryotic cells.

BACKGROUND OF THE INVENTION

Methods to control gene expression by silencing or suppressing a target gene include use of antisense, co-suppression, and RNA interference. Anti-sense gene suppression in plants is described by Shewmaker et al. in U.S. Pat. Nos. 5,107,065, 5,453,566, and 5,759,829. Gene suppression in bacteria using DNA which is complementary to mRNA encoding the gene to be suppressed is disclosed by Inouye et al. in U.S. Pat. Nos. 5,190,931, 5,208,149, and 5,272,065. RNA interference or double-stranded RNA-mediated gene suppression has been described by, e. g., Redenbaugh et al. in "Safety Assessment of Genetically Engineered Fruits and Vegetables", CRC Press, 1992; Chuang et al. (2000) *PNAS*, 97:4985-4990; and Wesley et al. (2001) *Plant J.*, 27:581-590.

In some cases, total or maximal silencing or suppression is desired, for example, where a suppression element is designed to suppress a pathogen target gene in order to achieve maximal protection of the host of that pathogen. However, complete suppression of a gene is not always preferred, for example, where complete suppression decreases viability or robustness of the organism in which the gene is silenced. In some cases, a desired phenotype (e. g., a particular level of a metabolite or a particular combination of traits) is associated with a specific level of suppression of a target gene. Thus, it is useful to be able to modify the level of silencing of a target gene or genes by a suppression element.

SUMMARY OF THE INVENTION

This invention discloses methods of controlling gene expression or gene suppression in eukaryotic cells. One aspect of the invention provides a method of modifying the degree of silencing of a target gene, including transcribing in a eukaryotic cell a modified suppression element, thereby obtaining a modified degree of silencing of the target gene, relative to a reference degree of silencing obtained through the transcription in the eukaryotic cell of a reference suppression element that corresponds to the target gene.

A second aspect of the invention provides a method of providing a eukaryotic cell having a desired phenotype resulting from transcription in the eukaryotic cell of a modified suppression element, including (a) providing a range of modified suppression elements, wherein each modified suppression element includes a fragment of a reference suppression element; (b) separately introducing each of the range of modified suppression elements into a eukaryotic cell, thereby producing a plurality of transgenic eukaryotic cells; (c) transcribing in each of the transgenic eukaryotic cell the modified suppression element therein introduced, and observing the resulting phenotype resulting from the transcribing; and (d) selecting from the plurality of transgenic eukaryotic cells at least one eukaryotic cell having the desired phenotype.

The invention further provides transgenic eukaryotic cells, and organisms containing such cells, having a phenotype resulting from suppression of a target gene by transcription in the eukaryotic cell of a modified suppression element. Further provided are transgenic plant cells, plants, and seeds containing modified suppression elements of the invention, and useful derivatives of such transgenic plant cells, plants, or seeds, such as food or feed products. Other specific embodiments of the invention are disclosed in the following detailed description.

DETAILED DESCRIPTION OF THE INVENTION

Figure 1:
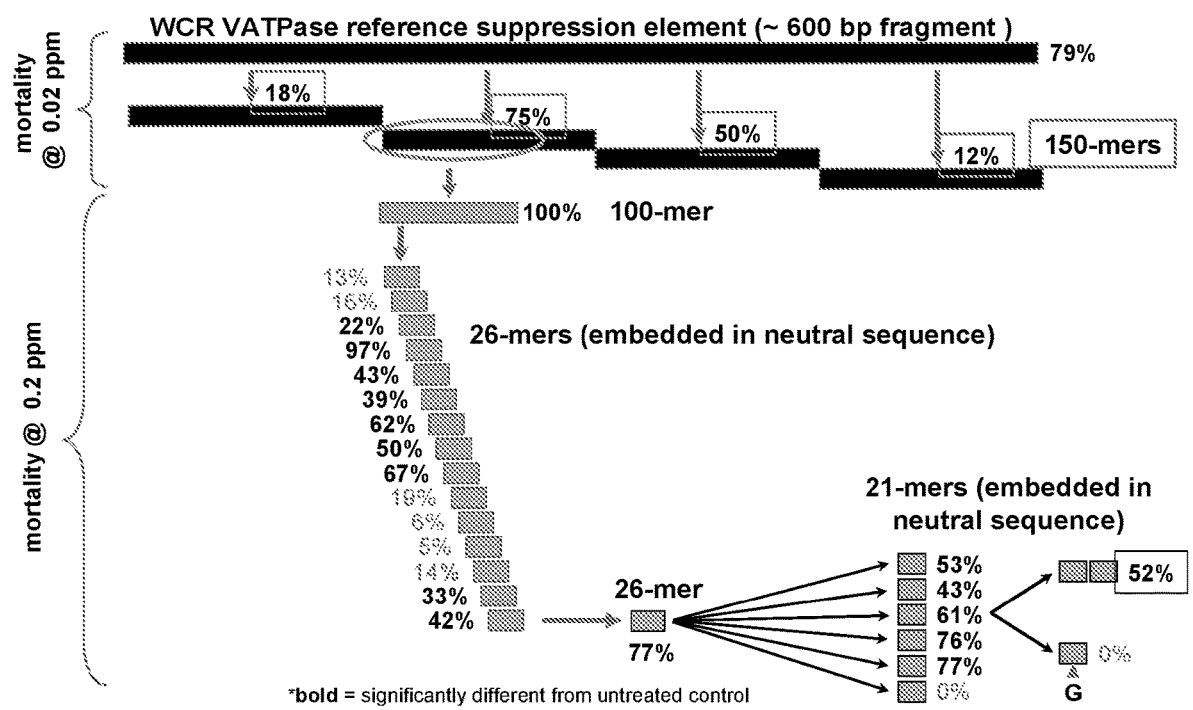
FIG. 1 schematically depicts a method for mapping silencing efficacy of a suppression element, useful in designing or selecting a modified suppression element, as described in Example 1.

Unless defined otherwise, all technical and scientific terms used herein have the same meaning as commonly understood by one of ordinary skill in the art to which this invention belongs. Generally, the nomenclature used herein and the manufacture or laboratory procedures described below are well known and commonly employed in the art. Conventional methods are used for these procedures, such as those provided in the art and various general references. Unless otherwise stated, nucleic acid sequences in the text of this specification are given, when read from left to right, in the 5' to 3' direction. Where a term is provided in the singular, the inventors also contemplate aspects of the invention described by the plural of that term. The nomenclature used herein and the laboratory procedures described below are those well known and commonly employed in the art. All of the United States Patents and United States Patent Application Publications cited in the description of the invention are herein incorporated by reference in their entirety. Where there are discrepancies in terms and definitions used in citations that are incorporated by reference, the terms used in this application shall have the definitions given herein. Other technical terms used herein have their ordinary meaning in the art that they are used, as exemplified by a variety of technical dictionaries. The inventors do not intend to be limited to a mechanism or mode of action. Reference thereto is provided for illustrative purposes only.

Method of Modifying Gene Silencing

In one aspect, this invention provides a method of modifying the degree of silencing of a target gene, including transcribing in a eukaryotic cell a modified suppression element, thereby obtaining a modified degree of silencing of the target gene, relative to a reference degree of silencing obtained through the transcription in the eukaryotic cell of a reference suppression element that corresponds to the target gene.

Eukaryotic Cells

The eukaryotic cell in which the suppression elements are to be transcribed can include any eukaryotic cell or cells. In preferred embodiments, the eukaryotic cell is selected from an animal cell and a plant cell. The eukaryotic cell can be a discrete cell (e. g., a plant, yeast, fungal, insect, or mammalian cell grown under cell culture conditions), a cell in undifferentiated tissue (e. g., a callus of undifferentiated plant cells), a cell in differentiated tissue, or a cell in an intact multicellular organism (such as a plant or an animal of any age or growth or reproductive stage).

Target Genes

The target gene to be silenced can include any gene, and can include multiple genes. The target gene can include a gene endogenous to the eukaryotic cell in which the suppression element is transcribed, such as a gene or genes native to the eukaryotic cell, or a transgene in a transgenic eukaryotic cell. The target gene can include a gene exogenous to the eukaryotic cell in which the suppression element is transcribed, for example, a gene native to a pest or pathogen or to a symbiont (e. g., a endobiont or an endocytobiont) of the eukaryotic cell.

The target gene can include a single gene or part of a single gene that is targetted for suppression, or can include, e. g., multiple consecutive segments of a target gene, multiple non-consecutive segments of a target gene, multiple alleles of a target gene, or multiple target genes from one or more species. In some embodiments, the target gene includes one contiguous nucleotide sequence. In other embodiments, the target gene includes non-contiguous nucleotide sequences, e. g., non-contiguous segments of a single mRNA transcript or non-contiguous segments of a native DNA nucleotide sequence (which can include coding DNA or non-coding DNA or a combination of both).

The target gene can be include nucleotides in translatable (coding) sequence, or nucleotides in non-coding sequence (such as non-coding regulatory sequence), or nucleotides in both coding and non-coding sequence. The target gene can include at least one eukaryotic target gene, at least one non-eukaryotic target gene, or both. A target gene can include any sequence from any species (including, but not limited to, non-eukaryotes such as bacteria and viruses; fungi; plants, including monocots and dicots, such as crop plants, ornamental plants, and non-domesticated or wild plants; prokaryotic or eukaryotic symbionts including intercellular symbionts (endobionts), intracellular symbionts (endocytobionts), and external symbionts (ectosymbionts); and invertebrates (e. g., arthropods, annelids, nematodes, and molluscs); and vertebrates (e.g., amphibians, fish, birds, domestic or wild mammals, and even humans).

Non-limiting examples of a target gene include non-translatable (non-coding) DNA, such as, but not limited to, 5' untranslated regions, promoters, enhancers, or other non-coding transcriptional regions, 3' untranslated regions, terminators, and introns. Target genes can also include genes encoding microRNAs, small interfering RNAs, RNA components of ribosomes or ribozymes, small nucleolar RNAs, and other non-coding RNAs (see, for example, non-coding RNA sequences described by Griffiths-Jones et al. (2005) *Nucleic Acids Res.*, 33:121-124, and non-coding RNAs which lack long open reading frames and function as ribo-regulators, as described by Erdmann et al. (2001) *Nucleic Acids Res.*, 29:189-193). One specific example of a target gene includes a microRNA recognition site (i.e., the site on an RNA strand to which a mature miRNA binds and induces cleavage). Another specific example of a target gene includes a microRNA precursor sequence, that is, the primary transcript encoding a microRNA, or the RNA intermediates processed from this primary transcript (e. g., a nuclear-limited pri-miRNA or a pre-miRNA which can be exported from the nucleus into the cytoplasm). See, for example, Lee et al. (2002) *EMBO Journal*, 21:4663-4670; Reinhart et al. (2002) *Genes & Dev.*, 16:161611626; Lund et al. (2004) *Science*, 303:95-98; and Millar and Waterhouse (2005) *Funct. Integr. Genomics*, 5:129-135. Target microRNA precursor DNA can be native to the transgenic plant of the invention, or can be native to a pest or pathogen of the transgenic plant. Target DNA can also include translatable (coding) sequence for genes encoding transcription factors and genes encoding enzymes involved in the biosynthesis or catabolism of molecules (such as, but not limited to, amino acids, fatty acids and other lipids, sugars and other carbohydrates, biological polymers, and secondary metabolites including alkaloids, terpenoids, polyketides, non-ribosomal peptides, and secondary metabolites of mixed biosynthetic origin). A target gene can be a native gene targetted for suppression, with or without concurrent expression (or suppression) of an exogenous transgene, e.g., by including a gene expression (or suppression) element in the same or in a separate recombinant DNA construct. For example, a native gene can be replaced with an exogenous transgene homologue.

In one embodiment, the suppression element is transcribed in a transgenic plant, and suppresses a target gene which is exogenous to the host plant but endogenous to a plant pest or pathogen (e. g., viruses, bacteria, fungi, and invertebrates such as insects, nematodes, and molluscs). Thus, in one embodiment the target gene is selected to provide resistance to a plant pest or pathogen, for example, resistance to a nematode such as soybean cyst nematode or root knot nematode or to a pest insect such as corn rootworm. Thus, target genes also include endogenous genes of plant pests and pathogens. Pest invertebrates include, but are not limited to, pest nematodes (e. g., cyst nematodes *Heterodera* spp. especially soybean cyst nematode *Heterodera glycines*, root knot nematodes *Meloidogyne* spp., lance nematodes *Hoplolaimus* spp., stunt nematodes *Tylenchorhynchus* spp., spiral nematodes *Helicotylenchus* spp., lesion nematodes *Pratylenchus* spp., ring nematodes *Criconema* spp., and foliar nematodes *Aphelenchus* spp. or *Aphelenchoides* spp.), pest molluscs (slugs and snails), and pest insects (e. g., corn rootworms, *Lygus* spp., aphids, corn borers, cutworms, armyworms, leafhoppers, Japanese beetles, grasshoppers, and other pest coleopterans, dipterans, and lepidopterans). Plant pathogens include fungi (e. g., the fungi that cause powdery mildew, rust, leaf spot and blight, damping-off, root rot, crown rot, cotton boll rot, stem canker, twig canker, vascular wilt, smut, or mold, including, but not limited to, *Fusarium* spp., *Phakospora* spp., *Rhizoctonia* spp., *Aspergillus* spp., *Gibberella* spp., *Pyricularia* spp., *Alternaria* spp., and *Phytophthora* spp.), bacteria (e. g., the bacteria that cause leaf spotting, fireblight, crown gall, and bacterial wilt), mollicutes (e. g., the mycoplasmas that cause yellows disease and spiroplasmas such as *Spiroplasma kunkelii*, which causes corn stunt), and viruses (e. g., the viruses that cause mosaics, vein banding, flecking, spotting, or abnormal growth). See also G. N. Agrios, "Plant Pathology" (Fourth Edition), Academic Press, San Diego, 1997, 635 pp., for descriptions of fungi, bacteria, mollicutes (including mycoplasmas and spiroplasmas), viruses, nematodes, parasitic higher plants, and flagellate protozoans, all of which are plant pests or pathogens. See also the continually updated compilation of plant pests and pathogens and the diseases caused by such on the American Phytopathological Society's "Common Names of Plant Diseases", compiled by the Committee on Standardization of Common Names for Plant Diseases of The American Phytopathological Society, 1978-2005.

Non-limiting examples of fungal plant pathogens of particular interest include *Phakospora pachirhizi* (Asian soy rust), *Puccinia sorghi* (corn common rust), *Puccinia polysora* (corn Southern rust), *Fusarium oxysporum* and other *Fusarium* spp., *Alternaria* spp., *Penicillium* spp., *Pythium aphanidermatum* and other *Pythium* spp., *Rhizoctonia solani*, *Exserohilum turcicum* (Northern corn leaf blight), *Bipolaris maydis* (Southern corn leaf blight), *Ustilago maydis* (corn smut), *Fusarium graminearum* (*Gibberella zeae*), *Fusarium verticilliodes* (*Gibberella moniliformis*), *F. proliferatum* (*G. fujikuroi* var. *intermedia*), *F. subglutinans* (*G. subglutinans*), *Diplodia maydis*, *Sporisorium holcisorghi*, *Colletotrichum graminicola*, *Setosphaeria turcica*, *Aureobasidium zeae*, *Phytophthora infestans*, *Phytophthora sojae*, *Sclerotinia sclerotiorum*, and the numerous fungal species provided in Tables 4 and 5 of U.S. Pat. No. 6,194,636, incorporated by reference.

Non-limiting examples of bacterial pathogens include *Pseudomonas avenae*, *Pseudomonas andropogonis*, *Erwinia stewartii*, *Pseudomonas syringae* pv. *syringae*, and the numerous bacterial species listed in Table 3 of U.S. Pat. No. 6,194,636, incorporated by reference.

Non-limiting examples of viral plant pathogens of particular interest include maize dwarf mosaic virus (MDMV), sugarcane mosaic virus (SCMV, formerly MDMV strain B), wheat streak mosaic virus (WSMV), maize chlorotic dwarf virus (MCDV), barley yellow dwarf virus (BYDV), banana bunchy top virus (BBTV), and the numerous viruses listed in Table 2 of U.S. Pat. No. 6,194,636, incorporated by reference.

Non-limiting examples of invertebrate pests include pests capable of infesting the root systems of crop plants, e. g., northern corn rootworm (*Diabrotica barberi*), southern corn rootworm (*Diabrotica undecimpunctata*), Western corn rootworm (*Diabrotica virgifera*), corn root aphid (*Anuraphis maidiradicis*), black cutworm (*Agrotis ipsilon*), glassy cutworm (*Crymodes devastator*), dingy cutworm (*Feltia ducens*), claybacked cutworm (*Agrotis gladiaria*), wireworm (*Melanotus* spp., *Aeolus mellillus*), wheat wireworm (*Aeolus mancus*), sand wireworm (*Horistonotus uhlerii*), maize billbug (*Sphenophorus maidis*), timothy billbug (*Sphenophorus zeae*), bluegrass billbug (*Sphenophorus parvulus*), southern corn billbug (*Sphenophorus callosus*), white grubs (*Phyllophaga* spp.), seedcorn maggot (*Delia platura*), grape colaspis (*Colaspis brunnea*), seedcorn beetle (*Stenolophus lecontei*), and slender seedcorn beetle (*Clivinia impressifrons*), as well as the parasitic nematodes listed in Table 6 of U.S. Pat. No. 6,194,636, incorporated by reference.

Target genes from pests can include invertebrate genes for major sperm protein, alpha tubulin, beta tubulin, vacuolar ATPase, glyceraldehyde-3-phosphate dehydrogenase, RNA polymerase II, chitin synthase, cytochromes, miRNAs, miRNA precursor molecules, miRNA promoters, as well as other genes such as those disclosed in Table II of United States Patent Application Publication 2004/0098761 A1, incorporated by reference. Target genes from pathogens can include genes for viral translation initiation factors, viral replicases, miRNAs, miRNA precursor molecules, fungal tubulin, fungal vacuolar ATPase, fungal chitin synthase, enzymes involved in fungal cell wall biosynthesis, cutinases, melanin biosynthetic enzymes, polygalacturonases, pectinases, pectin lyases, cellulases, proteases, and other genes involved in invasion and replication of the pathogen in the infected plant. Thus, a target gene need not be endogenous to the plant in which the suppression element is transcribed. A suppression element can be transcribed in a plant and used to suppress a gene of a pathogen or pest that may infest the plant.

Specific, non-limiting examples of suitable target genes also include amino acid catabolic genes (such as, but not limited to, the maize LKR/SDH gene encoding lysine-ketoglutarate reductase (LKR) and saccharopine dehydrogenase (SDH), and its homologues), maize zein genes, genes involved in fatty acid synthesis (e. g., plant microsomal fatty acid desaturases and plant acyl-ACP thioesterases, such as, but not limited to, those disclosed in U.S. Pat. Nos. 6,426,448, 6,372,965, and 6,872,872), genes involved in multi-step biosynthesis pathways, where it may be of interest to regulate the level of one or more intermediates, such as genes encoding enzymes for polyhydroxyalkanoate biosynthesis (see, for example, U.S. Pat. No. 5,750,848); and genes encoding cell-cycle control proteins, such as proteins with cyclin-dependent kinase (CDK) inhibitor-like activity (see, for example, genes disclosed in International Patent Application Publication Number WO 05007829A2). Target genes include genes encoding undesirable proteins (e. g., allergens or toxins) or the enzymes for the biosynthesis of undesirable compounds (e. g., undesirable flavor or odor components). Thus, one embodiment of the invention is a transgenic plant or tissue of such a plant that is improved by the suppression of allergenic proteins or toxins, e. g., a peanut, soybean, or wheat kernel with decreased allergenicity. Target genes include genes involved in fruit ripening, such as polygalacturonase. Target genes include genes where expression is preferably limited to a particular cell or tissue or developmental stage, or where expression is preferably transient, that is to say, where constitutive or general suppression, or suppression that spreads through many tissues, is not necessarily desired. Thus, other examples of suitable target genes include genes encoding proteins that, when expressed in transgenic plants, make the transgenic plants resistant to pests or pathogens (see, for example, genes for cholesterol oxidase as disclosed in U.S. Pat. No. 5,763,245); genes where expression is pest- or pathogen-induced; and genes which can induce or restore fertility (see, for example, the barstar/barnase genes described in U.S. Pat. No. 6,759,575).

Suppression Elements

The suppression elements of use in the method can be any suppression element (or combination of elements) that, when transcribed in the eukaryotic cell, results in silencing of the target gene. The suppression element can be transcribable DNA of any suitable length, and will generally include at least about 19 to about 27 nucleotides (for example 19, 20, 21, 22, 23, or 24 nucleotides) for every target gene. In many embodiments the suppression element includes more than 23 nucleotides (for example, more than about 30, about 50, about 100, about 200, about 300, about 500, about 1000, about 1500, about 2000, about 3000, about 4000, or about 5000 nucleotides) for every target gene intended to be suppressed. In some preferred embodiments, the suppression element includes "sense" sequence (i. e., nucleotide sequence that is identical or substantially identical to at least one contiguous segment of the sequence of the gene targetted for suppression), or "anti-sense" sequence (i.e., nucleotide sequence that is complementary or substantially complementary to or that forms Watson-Crick base pairs with at least one contiguous segment of the sequence of the gene targetted for suppression), or both sense and anti-sense sequence. In many preferred embodiments, the modified and reference suppression elements transcribe to at least partially double-stranded RNA. Suitable gene suppression elements are described in detail in U. S. Patent Application Publication 2006/0200878, incorporated by reference, and can be of any one or more types, including:

(a) DNA that includes at least one anti-sense DNA segment that is anti-sense to at least one segment of the target gene;
(b) DNA that includes multiple copies of at least one anti-sense DNA segment that is anti-sense to at least one segment of the target gene;
(c) DNA that includes at least one sense DNA segment that is at least one segment of the target gene;
(d) DNA that includes multiple copies of at least one sense DNA segment that is at least one segment of the target gene;
(e) DNA that transcribes to RNA for suppressing the target gene by forming double-stranded RNA and includes at least one anti-sense DNA segment that is anti-sense to at least one segment of the target gene and at least one sense DNA segment that is at least one segment of the target gene;
(f) DNA that transcribes to RNA for suppressing the target gene by forming a single double-stranded RNA and includes multiple serial anti-sense DNA segments that are anti-sense to at least one segment of the target gene and multiple serial sense DNA segments that are at least one segment of the target gene;
(g) DNA that transcribes to RNA for suppressing the target gene by forming multiple double strands of RNA and includes multiple anti-sense DNA segments that are anti-sense to at least one segment of the target gene and multiple sense DNA segments that are at least one segment of the target gene, and wherein the multiple anti-sense DNA segments and the multiple sense DNA segments are arranged in a series of inverted repeats;
(h) DNA that includes nucleotides derived from a plant miRNA;
(i) DNA that includes nucleotides of a siRNA;
(j) DNA that transcribes to an RNA aptamer capable of binding to a ligand; and
(k) DNA that transcribes to an RNA aptamer capable of binding to a ligand, and DNA that transcribes to regulatory RNA capable of regulating expression of the target gene, wherein the regulation is dependent on the conformation of the regulatory RNA, and the conformation of the regulatory RNA is allosterically affected by the binding state of the RNA aptamer.

Any of these suppression elements can be designed to suppress more than one target gene, including, for example, more than one allele of a target gene, multiple target genes (or multiple segments of at least one target gene) from a single species, or target genes from different species.

Where the suppression element includes multiple copies of anti-sense or multiple copies of sense DNA sequence, these multiple copies can be arranged serially in tandem repeats. In some embodiments, these multiple copies can be arranged serially end-to-end, that is, in directly connected tandem repeats. In some embodiments, these multiple copies can be arranged serially in interrupted tandem repeats, where one or more spacer DNA segments can be located adjacent to one or more of the multiple copies. Tandem repeats, whether directly connected or interrupted or a combination of both, can include multiple copies of a single anti-sense or multiple copies of a single sense DNA sequence in a serial arrangement or can include multiple copies of more than one anti-sense DNA sequence or of more than one sense DNA sequence in a serial arrangement. Where the suppression element includes multiple copies, the degree of complementarity can be, but need not be, identical for all of the multiple copies.

Generally, the reference suppression element and the modified suppression element are of similar types, e. g., both the reference suppression element and the modified suppression element include DNA that transcribes to RNA for suppressing the target gene by forming double-stranded RNA and includes at least one anti-sense DNA segment that is anti-sense to at least one segment of the target gene and at least one sense DNA segment that is at least one segment of the target gene. However, in some embodiments the modified suppression element and reference suppression element may be of different types, e. g., the reference suppression element includes an antisense DNA segment that is anti-sense to one or more segments of the target gene, whereas the modified suppression element includes multiple copies of the same or modified anti-sense DNA segment.

In those embodiments wherein the suppression element includes either at least one anti-sense DNA segment that is anti-sense to at least one segment of the at least one target gene or at least one sense DNA segment that is at least one segment of the at least one target gene, RNA transcribed from either the at least one anti-sense or at least one sense DNA can become double-stranded by the action of an RNA-dependent RNA polymerase (see, for example, U.S. Pat. No. 5,283,184). The double-stranded RNA can be in the form of a single dsRNA "stem" (region of base-pairing between sense and anti-sense strands), or can have multiple dsRNA "stems". Such multiple dsRNA "stems" can further be arranged in series or clusters to form tandem inverted repeats, or structures resembling "hammerhead" or "cloverleaf" shapes. Any of these suppression elements can further include spacer DNA segments found within a dsRNA "stem" (for example, as a spacer between multiple anti-sense or sense DNA segments or as a spacer between a base-pairing anti-sense DNA segment and a sense DNA segment) or outside of a double-stranded RNA "stem" (for example, as a loop region separating a pair of inverted repeats). In cases where base-pairing anti-sense and sense DNA segment are of unequal length, the longer segment can act as a spacer.

The suppression element can include spacer DNA, which can be virtually any DNA (such as, but not limited to, translatable DNA sequence encoding a gene, translatable DNA sequence encoding a marker or reporter gene; transcribable DNA derived from an intron, which upon transcription can be excised from the resulting transcribed RNA; transcribable DNA sequence encoding RNA that forms a structure such as a loop or stem or an aptamer capable of binding to a specific ligand; spliceable DNA such as introns and self-splicing ribozymes; transcribable DNA encoding a sequence for detection by nucleic acid hybridization, amplification, or sequencing; and a combination of these). Spacer DNA can be found, for example, between parts of a suppression element, or between different suppression elements. In some embodiments, spacer DNA is itself sense or anti-sense sequence of the target gene. In some preferred embodiments, the RNA transcribed from the spacer DNA (e. g., a large loop of antisense sequence of the target gene or an aptamer) assumes a secondary structure or threedimensional configuration that confers on the transcript a desired characteristic, such as increased stability, increased half-life in vivo, or cell or tissue specificity.

In a further embodiment, the suppression element can include DNA that includes nucleotides derived from a miRNA (microRNA), that is, a DNA sequence that corresponds to a miRNA native to a virus or a eukaryote (including plants and animals, especially invertebrates), or a DNA sequence derived from such a native miRNA but modified to include nucleotide sequences that do not correspond to the native miRNA. A particularly preferred embodiment includes a suppression element containing DNA that includes nucleotides derived from a viral or plant miRNA. A further embodiment includes a suppression element with DNA sequence that corresponds to a miRNA that is native to a fungus.

In a non-limiting example, the nucleotides derived from a miRNA can include DNA that includes nucleotides corresponding to the loop region of a native miRNA and nucleotides that are selected from a target gene sequence. In another non-limiting example, the nucleotides derived from a miRNA can include DNA derived from a miRNA precursor sequence, such as a native pri-miRNA or pre-miRNA sequence, or nucleotides corresponding to the regions of a native miRNA and nucleotides that are selected from a target gene sequence number such that the overall structure (e. g., the placement of mismatches in the stem structure of the pre-miRNA) is preserved to permit the pre-miRNA to be processed into a mature miRNA. In yet another embodiment, the suppression element can include DNA that includes nucleotides derived from a miRNA and capable of inducing or guiding in-phase cleavage of an endogenous transcript into trans-acting siRNAs, as described by Allen et al. (2005) *Cell,* 121:207-221. Thus, the DNA that includes nucleotides derived from a miRNA can include sequence naturally occurring in a miRNA or a miRNA precursor molecule, synthetic sequence, or both.

In preferred embodiments, the suppression element is included in a recombinant DNA construct that is useful in producing a transgenic eukaryotic cell. Generally, such a construct includes a promoter that is able to initiate transcription in the eukaryotic cell, and that is operably linked, directly or with intervening sequences, to the suppression element. The construct can optionally include a terminator element.

Where the recombinant DNA construct is to be transcribed in an animal cell, the promoter element is functional in an animal. Where the recombinant DNA construct is to be transcribed in a plant cell, the promoter element is functional in a plant. In various embodiments, the promoter element can include a promoter selected from the group consisting of a constitutive promoter, a spatially specific promoter, a temporally specific promoter, a developmentally specific promoter, and an inducible promoter. Where transcription of the construct is to occur in a plant cell, spatially specific promoters can include organelle-, cell-, tissue-, or organ-specific promoters functional in a plant (e. g., a plastid-specific, a root-specific, a pollen-specific, or a seed-specific promoter for expression in plastids, roots, pollen, or seeds, respectively). In many cases a seed-specific, embryo-specific, aleurone-specific, or endosperm-specific promoter is especially useful. Where transcription of the construct is to occur in an animal cell, spatially specific promoters include promoters that have enhanced activity in a particular animal cell or tissue (e. g., enhanced or specific promoter activity in nervous tissue, liver, muscle, eye, blood, marrow, breast, prostate, gonads, or other tissues). Temporally specific promoters can include promoters that tend to promote expression during certain developmental stages in an animal or plant's growth or reproductive cycle, or during different times of day or night, or at different seasons in a year. Inducible promoters include promoters induced by chemicals (e. g., exogenous or synthetic chemicals as well as endogenous pheromones and other signaling molecules) or by environmental conditions such as, but not limited to, biotic or abiotic stress (e. g., water deficit or drought, heat, cold, high or low nutrient or salt levels, high or low light levels, or pest or pathogen infection). An expression-specific promoter can also include promoters that are generally constitutively expressed but at differing degrees or "strengths" of expression, including promoters commonly regarded as "strong promoters" or as "weak promoters". The promoter element can include nucleic acid sequences that are not naturally occurring promoters or promoter elements or homologues thereof but that can regulate expression of a gene. Examples of such "gene independent" regulatory sequences include naturally occurring or artificially designed RNA sequences that include a ligand-binding region or aptamer and a regulatory region (which can be cis-acting). See, for example, the discussion of RNA regulatory elements ("riboregulators") given by Isaacs et al. (2004) *Nat. Biotechnol.,* 22:841-847, Bayer and Smolke (2005) *Nature Biotechnol.,* 23:337-343, Mandal and Breaker (2004) *Nature Rev. Mol. Cell Biol.,* 5:451-463, Davidson and Ellington (2005) *Trends Biotechnol.,* 23:109-112, Winkler et al. (2002) *Nature,* 419:952-956, Sudarsan et al. (2003) *RNA,* 9:644-647, and Mandal and Breaker (2004) *Nature Struct. Mol. Biol.,* 11:29-35. Such "riboregulators" could be selected or designed for specific spatial or temporal specificity, for example, to regulate translation of the exogenous gene only in the presence (or absence) of a given concentration of the appropriate ligand.

In some embodiments, a recombinant DNA construct containing the suppression element includes both a promoter element and a functional terminator element. Where it is functional, the terminator element includes a functional polyadenylation signal and polyadenylation site, allowing RNA transcribed from the recombinant DNA construct to be polyadenylated and processed for transport into the cytoplasm. In other embodiments, a functional terminator element is absent. In some embodiments where a functional terminator element is absent, at least one of a functional polyadenylation signal and a functional polyadenylation site is absent. In other embodiments, a 3' untranslated region is absent. In these cases, the recombinant DNA construct is transcribed as unpolyadenylated RNA and is preferably not transported into the cytoplasm.

In some embodiments, the suppression element is embedded within an intron, which is preferably an intron flanked on one or on both sides by non-protein-coding DNA. One non-limiting embodiment is a recombinant DNA construct that consists entirely of non-coding DNA and that includes the suppression element (or elements) embedded within an intron. Introns suitable for use in constructs of the invention can be viral introns (e. g., Yamada et al. (1994) *Nucleic Acids Res.,* 22:2532-2537), eukaryotic introns (including animal, fungal, and plant introns), archeal or bacterial introns (e. g., Belfort et al. (1995) *J. Bacteriol.,* 177:3897-3903), or any naturally occurring or artificial (e. g., Yoshimatsu and Nagawa (1989) *Science,* 244:1346-1348) DNA sequences with intron-like functionality in the plant in which the recombinant DNA construct of the invention is to be transcribed. While essentially any intron can be used in the practice of this invention as a host for embedded DNA, particularly preferred are introns that are introns that enhance expression in a plant or introns that are derived from a 5' untranslated leader sequence. Where a recombinant DNA construct of the invention is used to transform a plant, plant-sourced introns can be especially preferred. Examples of especially preferred plant introns include a rice actin 1 intron (I-Os-Act1) (Wang et al. (1992) *Mol. Cell Biol.,* 12:3399-3406; McElroy et al. (1990) *Plant Cell,* 2:163-171), a maize heat shock protein intron (I-Zm-hsp70) (U.S. Pat. Nos. 5,593,874 and 5,859,347), and a maize alcohol dehydrogenase intron (I-Zm-adh1) (Callis et al. (1987) *Genes Dev.,* 1:1183-1200). Other examples of introns suitable for use in the invention include the tobacco mosaic virus 5' leader sequence or "omega" leader (Gallie and Walbot (1992) *Nucleic Acids Res.,* 20:4631-4638), the Shrunken-1 (Sh-1) intron (Vasil et al. (1989) *Plant Physiol.,* 91:1575-1579), the maize sucrose synthase intron (Clancy and Hannah (2002) *Plant Physiol.,* 130:918-929), the heat shock protein 18 (hsp18) intron (Silva et al. (1987) *J. Cell Biol.,* 105:245), and the 82 kilodalton heat shock protein (hsp82) intron (Semrau et al. (1989) J. Cell Biol., 109, p. 39A, and Mettler et al. (May 1990) N.A.T.O. Advanced Studies Institute on Molecular Biology, Elmer, Bavaria).

In some embodiments, the suppression element is included in a recombinant DNA construct that also includes at least one expression element (e. g., to express a gene of interest, a reporter gene, or a marker gene) or additional suppression elements.

Reference Suppression Elements and Modified Suppression Elements

The reference suppression element is any suppression element (see "Suppression Elements" beginning at paragraph 0025 above) used to establish a reference degree of silencing (see "Degrees of Silencing" beginning at paragraph 0050 below). The modified suppression element is any suppression element that is different but derived from the reference suppression element. Thus, modification of the reference suppression element to obtain one or more modified suppression elements can involve changing the reference suppression element's size (e. g., by fragmentation or truncation), changing the reference suppression element's nucleotide sequence (e. g., by substitution or deletion of nucleotides), changing the arrangement of the order and/or number of reference suppression fragments, changing the reference suppression element's orientation (sense or anti-sense) or position in a recombinant DNA construct, or inclusion or deletion of stabilizing or destabilizing elements.

In one embodiment, the modified suppression element includes at least one fragment of the reference suppression element. In some embodiments, the modified suppression element includes multiple fragments of the reference suppression element, which can be multiple different fragments of the reference suppression element or multiple copies of one or more fragments of the reference suppression element. Where the modified suppression elements includes multiple different fragments of the reference suppression element, the multiple different fragments can be in the same order as, or in an order different from, that in which they are arranged in the reference suppression element. In another embodiment, the modified suppression element is obtained by modification of the suppression element to target one or more fragments (e. g., truncations) of the target gene At least one fragment of the reference suppression element may be provided in a cell by any suitable means. In one embodiment, the at least one fragment is obtained by truncation of the reference suppression element. Such truncation includes deletion of one or more nucleotides from the 5' end, from the 3' end, or from both the 5' and 3' ends of the reference suppression element. In another embodiment, the at least one fragment is provided by deletion of one or more internal (non-terminal) nucleotides from the reference suppression element. Deletion can be of a single sequence of contiguous nucleotides from the reference suppression element, or of multiple such sequences.

Generally, the at least one fragment is at least 19 contiguous nucleotides in length, but the fragment can be any length necessary to obtain the desired degree of silencing, e. g., at least 21, at least 22, at least 23, or at least 24 nucleotides. In some embodiments, the fragment can include more than about 25, about 50, about 75, about 100, about 150, about 200, about 300, or about 500 nucleotides or greater. In comparison to the length of the reference suppression element, the at least one fragment can include between about 1% to about 98%, e. g., about 98%, about 95%, about 90%, about 85%, about 80%, about 70%, about 60%, about 50%, about 40%, about 30%, about 20%, about 10%, about 5%, or about 1% of the length of the reference suppression element. The at least one fragment can be less than 1% of the length of the reference suppression element.

In one embodiment of the method, the modified suppression element is selected by mapping the silencing efficacy for the target gene. Mapping can involve predictive methods or empirical determination of silencing efficacy. Predictive methods include, e. g., use of the criteria for predicting the efficiency at which a given siRNA would function as identified by Reynolds et al. (2004) *Nature Biotechnol.,* 22:326-330, and further described in United States Patent Application Publication 2005/0255487, which is incorporated by reference. In one embodiment, mapping consists primarily or entirely of empirical determination of silencing efficacy. Empirical determination of silencing efficacy can include determining actual gene silencing (e. g., by measuring mRNA or protein expression levels of the target gene or its encoded product), or any suitable proxy measurement. Proxy measurements can include, for example, measuring a trait or phenotype that results from expression of the target gene (e. g., measuring the level of a metabolic product, a measurable phenotype of a transgenic organism such as growth rate or yield or pest resistance of a transgenic plant).

Mapping can be carried out at any suitable resolution (in terms of nucleotide length of a potential suppression element) of the target gene. In general, fine mapping includes determination and/or prediction of efficacy of a minimum suppression element size, e. g., at least 19 contiguous nucleotides in length, or at least 21, at least 22, at least 23, or at least 24 nucleotides in length. However, mapping can be carried out for any length of suppression element, including suppression elements that are larger than the reference suppression element.

In one embodiment, the modified selection element is further selected or adapted to avoid silencing of non-target genes, or to avoid generation of undesirable polypeptides, or both. Non-target genes can include any gene not intended to be silenced or suppressed, in the eukaryotic cell in which the suppression element is transcribed or in organisms that may come into contact with the transcribed suppression element or its products. In some embodiments (for example, where the suppression element is intended to have applications across multiple species), it can be desirable for the suppression element to include sequence common to multiple species in which the target gene is to be silenced. Thus, the suppression element can include nucleotide sequence selected to be specific for one taxon (for example, specific to a genus, family, or even a larger taxon such as a phylum, e. g., arthropoda) but not for other taxa (for example, plants or vertebrates or mammals). In one non-limiting example, a suppression element includes nucleotide sequence for dsRNA-mediated gene silencing in corn rootworm that is selected to be specific to all members of the genus *Diabrotica*. In a further example, such a *Diabrotica*-targetted suppression element is selected so as to not contain nucleotide sequence from beneficial coleopterans (for example, predatory coccinellid beetles, commonly known as ladybugs or ladybirds) or other beneficial insect species.

In another embodiment, the modified suppression element is further selected or adapted to avoid generation of undesirable polypeptides. For example, a suppression element can be screened to eliminate or minimize sequences that encode known undesirable polypeptides or close homologues of these. Undesirable polypeptides include, but are not limited to, polypeptides homologous to known allergenic polypeptides and polypeptides homologous to known polypeptide toxins. Sequences encoding such undesirable potentially allergenic peptides are known in the art (e. g., Gendel (1998) *Adv. Food Nutr. Res.*, 42:63-92) and are publicly available, for example, at the Food Allergy Research and Resource Program (FARRP) allergen database or the Biotechnology Information for Food Safety Databases. Undesirable sequences can also include, for example, those polypeptide sequences annotated as known toxins or as potential or known allergens and contained in publicly available databases such as GenBank, EMBL, SwissProt, and others, which are searchable by the Entrez system. Non-limiting examples of undesirable, potentially allergenic peptide sequences include glycinin from soybean, oleosin and agglutinin from peanut, glutenins from wheat, casein, lactalbumin, and lactoglobulin from bovine milk, and tropomyosin from various shellfish. Non-limiting examples of undesirable, potentially toxic peptides include tetanus toxin tetA from *Clostridium tetani*, diarrheal toxins from *Staphylococcus aureus*, and venoms such as conotoxins from *Conus* spp. and neurotoxins from arthropods and reptiles.

In one non-limiting example, potential suppression element sequences were screened to eliminate those sequences encoding polypeptides with perfect homology to a known allergen or toxin over 8 contiguous amino acids, or with at least 35% identity over at least 80 amino acids; such screens can be performed on any and all possible reading frames in both directions, on potential open reading frames that begin with ATG, or on all possible reading frames, regardless of whether they start with an ATG or not.

In a non-limiting example, screens (referred to as "EAT/Tox" screens) were routinely performed on the transcribed portions of suppression elements that are intended to produce a double stranded RNA but are not intended to be translated into a polypeptide. These screens can be performed on any and all possible reading frames in both directions, and on potential open reading frames that begin with ATG, or on all possible reading frames, regardless of whether they start with an ATG or not. When a "hit" or match is made, that is, when a sequence that encodes a potential polypeptide with perfect homology to a known allergen or toxin over 8 contiguous amino acids (or at least about 35% identity over at least about 80 amino acids), is identified, the nucleotide sequences corresponding to the hit can be avoided, eliminated, or modified when selecting a suppression element.

Avoiding, elimination of, or modification of, an undesired sequence may be achieved by any of a number of methods known to those skilled in the art. In some cases, the result may be novel sequences that are believed to not exist naturally. For example, avoiding certain sequences can be accomplished by joining together "clean" sequences into novel chimeric suppression element that will produce a novel transcript, most preferably a transcript that provides the desired modified level of suppression.

Applicants recognize that it is possible for suppression element sequences that imperfectly correspond to the intended target gene to be effective at gene silencing. For example, it has been shown that mismatches near the center of a miRNA complementary site has stronger effects on the miRNA's gene silencing than do more distally located mismatches (see, for example, FIG. 4 in Mallory et al. (2004) *EMBO J.*, 23:3356-3364). In another example, it has been reported that, both the position of a mismatched base pair and the identity of the nucleotides forming the mismatch influence the ability of a given siRNA to silence a target gene, and that adenine-cytosine mismatches, in addition to the G:U wobble base pair, were well tolerated, as described by Du et al. (2005) *Nucleic Acids Res.*, 33:1671-1677. Thus, a suppression element need not always have 100% sequence identity with (or 100% complementary to) the intended target gene, but generally would preferably have substantial sequence identity (or complementarity) with the intended target gene, such as about 95%, about 90%, about 85%, or about 80% sequence identity with (or complementarity to) the intended target gene. One skilled in the art would be capable of judging the importance given to screening for regions predicted to be more highly specific to the target gene or predicted to not generate undesirable polypeptides, relative to the importance given to other criteria, such as, but not limited to, the percent sequence identity with the intended target gene or the predicted or empirically determined silencing efficacy of a given suppression element. For example, it may be desirable for a given suppression element to be active across several species, and therefore one skilled in the art may determine that it is more important to include regions specific to the several species of interest, but less important to screen for regions predicted to have higher gene silencing efficiency or for regions predicted to generate undesirable polypeptides.

Degrees of Silencing

Transcription in the eukaryotic cell of a reference suppression element (see "Reference Suppression Elements and Modified Suppression Elements" beginning at paragraph 0038 above) that targets a given target gene preferably results in the suppression of expression of the target gene at a certain level (termed the "reference degree of silencing"), relative to the level of expression of the target gene in the absence of such transcription. The reference degree of silencing is not an absolute level of suppression but rather is a level of suppression selected as a benchmark for comparison with the level of suppression by alternative suppression elements. Thus, the reference degree of silencing of the target gene can be any level of suppression, from about zero suppression (relative to expression in the absence of transcription of the reference suppression element) to about complete suppression, or any level in between, and the degree of silencing can be selected as described herein to achieve a desired level of modulation of expression of the targetted sequence (or target gene). Use of the term "reference degree of silencing" in this context is not meant to imply a "maximum" or "optimal" degree of silencing.

Transcription in the eukaryotic cell of a modified suppression element (see "Reference Suppression Elements and Modified Suppression Elements" beginning at paragraph 0038 above) preferably results in a level of suppression of expression of the target gene that differs from that obtained by transcription of the reference suppression element, wherein such level of suppression is termed the "modified degree of silencing". In some embodiments, the modified degree of silencing is increased silencing of the target gene, relative to the reference degree of silencing. In other embodiments, the modified degree of silencing is decreased silencing of the target gene, relative to the reference degree of silencing.

Detecting or measuring the degree of silencing of a target gene resulting from transcription of the suppression element can be achieved by any suitable method to detect the expression (or suppression) of DNA sequence or the RNA transcript corresponding to the target gene, or of a peptide encoded by the target gene. Suitable methods include protein detection methods (e. g., western blots, ELISAs, and other immunochemical methods, and measurements of enzymatic activity), or nucleic acid detection methods (e. g., Southern blots, northern blots, PCR, RT-PCR, fluorescent in situ hybridization, and TaqMAN assays). Such methods are well known to those of ordinary skill in the art as evidenced by the numerous handbooks available; see, for example, Joseph Sambrook and David W. Russell, "Molecular Cloning: A Laboratory Manual" (third edition), Cold Spring Harbor Laboratory Press, N Y, 2001; Frederick M. Ausubel et al. (editors) "Short Protocols in Molecular Biology" (fifth edition), John Wiley and Sons, 2002; John M. Walker (editor) "Protein Protocols Handbook" (second edition), Humana Press, 2002; and Leandro Peña (editor) "Transgenic Plants: Methods and Protocols", Humana Press, 2004.

Other suitable methods for detecting or measuring suppression of a target gene include measurement of any other trait that is a proxy (surrogate) indication of gene suppression in the eukaryotic cell in which the suppression element is transcribed, relative to a cell in which the modified or reference suppression element is not transcribed. Such proxy indications include, e. g., gross or microscopic morphological traits, growth rates, yield, reproductive or recruitment rates, resistance to pests or pathogens, or resistance to biotic or abiotic stress (e. g., water deficit stress, salt stress, nutrient stress, heat or cold stress). Proxy measurements of gene suppression include measurements of a phenotypic trait (e. g., growth rates, levels of a metabolite in a tissue, mortality in animals in which an animal target gene is suppressed) and in vitro assays (e. g., plant part assays such as leaf or root assays to indicate tolerance of abiotic stress).

Method of Providing a Desired Trait in a Eukaryote

In another aspect, the invention provides a method of providing a eukaryotic cell having a desired phenotype resulting from transcription in the eukaryotic cell of a modified suppression element, including (a) providing a range of modified suppression elements, wherein each modified suppression element includes a fragment of a reference suppression element; (b) separately introducing each of the range of modified suppression elements into a eukaryotic cell, thereby producing a plurality of transgenic eukaryotic cells; (c) transcribing in each of the transgenic eukaryotic cell the modified suppression element therein introduced, and observing the resulting phenotype resulting from the transcribing; and (d) selecting from the plurality of transgenic eukaryotic cells at least one eukaryotic cell having the desired phenotype.

The range of modified suppression elements includes any suitable number of modified suppression elements of one or more suppression element types as described under "Suppression Elements" (beginning at paragraph 0025 above) and "Reference Suppression Elements and Modified Suppression Elements" (beginning at paragraph 0038 above).

In one embodiment, the eukaryotic cell includes a transgenic plant cell. In some embodiments, the method further includes growing a transgenic plant including the transgenic plant cell. Suitable techniques for producing a transgenic plant including the transgenic plant cell are described under "Making and Using Transgenic Plant Cells and Transgenic Plants" beginning at paragraph 0057 below.

Making and Using Transgenic Plant Cells and Transgenic Plants

In preferred embodiments of the invention, the suppression is transcribed in a transgenic plant cell. The transgenic plant cell can be an isolated plant cell (e. g., individual plant cells or cells grown in or on an artificial culture medium), or can be a plant cell in undifferentiated tissue (e. g., callus or any aggregation of plant cells). The transgenic plant cell can be a plant cell in at least one differentiated tissue selected from the group consisting of leaf (e. g., petiole and blade), root, stem (e. g., tuber, rhizome, stolon, bulb, and corm) stalk (e. g., xylem, phloem), wood, seed, fruit (e. g., nut, grain, fleshy fruits), and flower (e. g., stamen, filament, anther, pollen, carpel, pistil, ovary, ovules). The invention further provides a transgenic plant having in its genome any of the reference or modified suppression elements (or recombinant DNA constructs including the reference or modified suppression element) presently disclosed, including a regenerated plant prepared from the transgenic plant cells disclosed and claimed herein, or a progeny plant (which can be a hybrid progeny plant) of the regenerated plant, or seed of such a transgenic plant. Also provided is a transgenic seed having in its genome any of the reference or modified suppression elements or recombinant DNA constructs presently disclosed, and a transgenic plant grown from such transgenic seed.

The transgenic plant cell or plant of the invention can be any plant cell or plant. Stably transformed transgenic plants are particularly preferred. In many preferred embodiments, the transgenic plant is a fertile transgenic plant from which seed can be harvested, and thus the invention further claims seed of such transgenic plants, wherein the seed is preferably also transgenic, that is, preferably contains the reference or modified suppression elements or recombinant DNA constructs of the invention.

Where a recombinant DNA construct is used to produce a transgenic plant cell or transgenic plant of the invention, the transformation can include any of the well-known and demonstrated methods and compositions. Suitable methods for plant transformation include virtually any method by which DNA can be introduced into a cell, such as by direct delivery of DNA (e. g., by PEG-mediated transformation of protoplasts, by electroporation, by agitation with silicon carbide fibers, and by acceleration of DNA coated particles), by *Agrobacterium*-mediated transformation, by viral or other vectors, etc. One preferred method of plant transformation is microprojectile bombardment, for example, as illustrated in U.S. Pat. No. 5,015,580 (soy), U.S. Pat. No. 5,550,318 (maize), U.S. Pat. No. 5,538,880 (maize), U.S. Pat. No. 6,153,812 (wheat), U.S. Pat. No. 6,160,208 (maize), U.S. Pat. No. 6,288,312 (rice), U.S. Pat. No. 6,399,861 (maize), and U.S. Pat. No. 6,403,865 (maize).

Another preferred method of plant transformation is *Agrobacterium*-mediated transformation. In one preferred embodiment of the invention, the transgenic plant cell of the invention is obtained by transformation by means of *Agrobacterium* containing a binary Ti plasmid system, wherein the *Agrobacterium* carries a first Ti plasmid and a second, chimeric plasmid containing at least one T-DNA border of a wild-type Ti plasmid, a promoter functional in the transformed plant cell and operably linked to a gene suppression construct of the invention. See, for example, U.S. Pat. No. 5,159,135; De Framond (1983) Biotechnology, 1:262-269; and Hoekema et al., (1983) Nature, 303:179. In such a binary system, the smaller plasmid, containing the T-DNA border or borders, can be conveniently constructed and manipulated in a suitable alternative host, such as *E. coli*, and then transferred into *Agrobacterium*.

Detailed procedures for *Agrobacterium*-mediated transformation of plants, especially crop plants, include, for example, procedures disclosed in U.S. Pat. Nos. 5,004,863, 5,159,135, and 5,518,908 (cotton); U.S. Pat. Nos. 5,416,011, 5,569,834, 5,824,877 and 6,384,301 (soy); U.S. Pat. No. 5,591,616 (maize); U.S. Pat. No. 5,981,840 (maize); and U.S. Pat. No. 5,463,174 (brassicas). Similar methods have been reported for, among others, peanut (Cheng et al. (1996) *Plant Cell Rep.*, 15: 653); asparagus (Bytebier et al. (1987) *Proc. Natl. Acad. Sci. U.S.A.*, 84:5345); barley (Wan and Lemaux (1994) *Plant Physiol.*, 104:37); rice (Toriyama et al. (1988) *Bio/Technology*, 6:10; Zhang et al. (1988) *Plant Cell Rep.*, 7:379; wheat (Vasil et al. (1992) *Bio/Technology*, 10:667; Becker et al. (1994) *Plant J.*, 5:299), and alfalfa (Masoud et al. (1996) *Transgen. Res.*, 5:313). See also United States Patent Application Publication 2003/0167537A1 for a description of vectors, transformation methods, and production of transformed *Arabidopsis thaliana* plants where transcription factors are constitutively expressed by a CaMV35S promoter. Transgenic plant cells and transgenic plants can also be obtained by transformation with other vectors, such as, but not limited to, viral vectors (e. g., tobacco etch potyvirus (TEV), barley stripe mosaic virus (BSMV), and the viruses referenced in Edwardson and Christie, "The Potyvirus Group: Monograph No. 16, 1991, Agric. Exp. Station, Univ. of Florida), plasmids, cosmids, YACs (yeast artificial chromosomes), BACs (bacterial artificial chromosomes) or any other suitable cloning vector used with an appropriate transformation protocol, e. g., bacterial infection (e. g., with *Agrobacterium* as described above), binary bacterial artificial chromosome constructs, direct delivery of DNA (e. g., via PEG-mediated transformation, desiccation/inhibition-mediated DNA uptake, electroporation, agitation with silicon carbide fibers, and microprojectile bombardment). It would be clear to one of skill in the art that various transformation methodologies can be used and modified for production of stable transgenic plants from any number of plant species.

Transformation methods to provide transgenic plant cells and transgenic plants containing stably integrated recombinant DNA are preferably practiced in tissue culture on media and in a controlled environment. "Media" refers to the numerous nutrient mixtures that are used to grow cells in vitro, that is, outside of the intact living organism. Recipient cell targets include, but are not limited to, meristem cells, callus, immature embryos or parts of embryos, and gametic cells such as microspores, pollen, sperm, and egg cells. It is contemplated that any cell from which a fertile plant can be regenerated can be useful as a recipient cell for practice of the invention. Callus can be initiated from various tissue sources, including, but not limited to, immature embryos or parts of embryos, seedling apical meristems, microspores, and the like. Those cells which are capable of proliferating as callus can serve as recipient cells for genetic transformation. Practical transformation methods and materials for making transgenic plants of this invention (e. g., various media and recipient target cells, transformation of immature embryos, and subsequent regeneration of fertile transgenic plants) are disclosed, for example, in U.S. Pat. Nos. 6,194,636 and 6,232,526 and United States Application Publication 2004/0216189.

In general transformation practice, DNA is introduced into only a small percentage of target cells in any one transformation experiment. Marker genes are generally used to provide an efficient system for identification of those cells that are stably transformed by receiving and integrating a transgenic DNA construct into their genomes. Preferred marker genes provide selective markers which confer resistance to a selective agent, such as an antibiotic or herbicide. Any of the antibiotics or herbicides to which a plant cell may be resistant can be a useful agent for selection. Potentially transformed cells are exposed to the selective agent. In the population of surviving cells will be those cells where, generally, the resistance-conferring gene is integrated and expressed at sufficient levels to permit cell survival. Cells can be tested further to confirm stable integration of the recombinant DNA. Commonly used selective marker genes include those conferring resistance to antibiotics such as kanamycin or paromomycin (nptII), hygromycin B (aph IV) and gentamycin (aac3 and aacC4) or resistance to herbicides such as glufosinate (bar or pat) and glyphosate (EPSPS). Examples of useful selective marker genes and selection agents are illustrated in U.S. Pat. Nos. 5,550,318, 5,633,435, 5,780,708, and 6,118,047. Screenable markers or reporters, such as markers that provide an ability to visually identify transformants can also be employed. Non-limiting examples of useful screenable markers include, for example, a gene expressing a protein that produces a detectable color by acting on a chromogenic substrate (e. g., beta-glucuronidase (GUS) (uidA) or luciferase (luc)) or that itself is detectable, such as green fluorescent protein (GFP) (gfp) or an immunogenic molecule. Those of skill in the art will recognize that many other useful markers or reporters are available for use.

The recombinant DNA constructs of the invention can be stacked with other recombinant DNA for imparting additional traits (e. g., in the case of transformed plants, traits including herbicide resistance, pest resistance, cold germination tolerance, water deficit tolerance, and the like) for example, by expressing or suppressing other genes. Constructs for coordinated decrease and increase of gene expression are disclosed in United States Patent Application Publication 2004/0126845 A1.

Seeds of transgenic, fertile plants can be harvested and used to grow progeny generations, including hybrid generations, of transgenic plants that include the reference or modified suppression elements or recombinant DNA constructs in their genome. Thus, in addition to direct transformation of a plant with a recombinant DNA construct, transgenic plants can be prepared by crossing a first plant having the reference or modified suppression elements or recombinant DNA constructs with a second plant lacking the reference or modified suppression elements or recombinant DNA constructs. For example, recombinant DNA can be introduced into a plant line that is amenable to transformation to produce a transgenic plant, which can be crossed with a second plant line to introgress the recombinant DNA into the resulting progeny. A transgenic plant with the reference or modified suppression elements or recombinant DNA constructs can be crossed with a plant line having other recombinant DNA that confers one or more additional trait(s) (such as, but not limited to, herbicide resistance, pest or disease resistance, environmental stress resistance, modified nutrient content, and yield improvement) to produce progeny plants having recombinant DNA that confers both the desired target sequence expression behavior and the additional trait(s).

Typically, in such breeding for combining traits the transgenic plant donating the additional trait is a male line and the transgenic plant carrying the base traits is the female line. The progeny of this cross segregate such that some of the plant will carry the DNA for both parental traits and some will carry DNA for one parental trait; such plants can be identified by markers associated with parental recombinant DNA Progeny plants carrying DNA for both parental traits can be crossed back into the female parent line multiple times, e. g., usually 6 to 8 generations, to produce a progeny plant with substantially the same genotype as one original transgenic parental line but for the recombinant DNA of the other transgenic parental line.

Yet another aspect of the invention is a transgenic plant grown from the transgenic seed of the invention. This invention contemplates transgenic plants grown directly from transgenic seed containing the reference or modified suppression elements or recombinant DNA constructs as well as progeny generations of plants, including inbred or hybrid plant lines, made by crossing a transgenic plant grown directly from transgenic seed to a second plant not grown from the same transgenic seed.

Crossing can include, for example, the following steps:
(a) plant seeds of the first parent plant (e. g., non-transgenic or a transgenic) and a second parent plant that is transgenic according to the invention;
(b) grow the seeds of the first and second parent plants into plants that bear flowers;
(c) pollinate a flower from the first parent with pollen from the second parent; and
(d) harvest seeds produced on the parent plant bearing the fertilized flower.

It is often desirable to introgress recombinant DNA into elite varieties, e. g., by backcrossing, to transfer a specific desirable trait from one source to an inbred or other plant that lacks that trait. This can be accomplished, for example, by first crossing a superior inbred ("A") (recurrent parent) to a donor inbred ("B") (non-recurrent parent), which carries the appropriate gene(s) for the trait in question, for example, a construct prepared in accordance with the current invention. The progeny of this cross first are selected in the resultant progeny for the desired trait to be transferred from the non-recurrent parent "B", and then the selected progeny are mated back to the superior recurrent parent "A". After five or more backcross generations with selection for the desired trait, the progeny are hemizygous for loci controlling the characteristic being transferred, but are like the superior parent for most or almost all other genes. The last backcross generation would be selfed to give progeny which are pure breeding for the gene(s) being transferred, i. e., one or more transformation events.

Through a series of breeding manipulations, a selected DNA construct can be moved from one line into an entirely different line without the need for further recombinant manipulation. One can thus produce inbred plants which are true breeding for one or more DNA constructs. By crossing different inbred plants, one can produce a large number of different hybrids with different combinations of DNA constructs. In this way, plants can be produced which have the desirable agronomic properties frequently associated with hybrids ("hybrid vigor"), as well as the desirable characteristics imparted by one or more DNA constructs.

Genetic markers can be used to assist in the introgression of one or more DNA constructs of the invention from one genetic background into another. Marker assisted selection offers advantages relative to conventional breeding in that it can be used to avoid errors caused by phenotypic variations. Further, genetic markers can provide data regarding the relative degree of elite germplasm in the individual progeny of a particular cross. For example, when a plant with a desired trait which otherwise has a non-agronomically desirable genetic background is crossed to an elite parent, genetic markers can be used to select progeny which not only possess the trait of interest, but also have a relatively large proportion of the desired germplasm. In this way, the number of generations required to introgress one or more traits into a particular genetic background is minimized. The usefulness of marker assisted selection in breeding transgenic plants of the current invention, as well as types of useful molecular markers, such as but not limited to SSRs and SNPs, are discussed in PCT Application Publication WO 02/062129 and United States Patent Application Publications Numbers 2002/0133852, 2003/0049612, and 2003/0005491.

In certain transgenic plant cells and transgenic plants of the invention, it may be desirable to concurrently express (or suppress) a gene of interest while also regulating expression of a target gene. Thus, in some embodiments, the transgenic plant contains recombinant DNA further including a gene expression (or suppression) element for expressing at least one gene of interest, and regulation of expression of a target gene is preferably effected with concurrent expression (or suppression) of the at least one gene of interest in the transgenic plant.

Thus, as described herein, the transgenic plant cells or transgenic plants can be obtained by use of any appropriate transient or stable, integrative or non-integrative transformation method known in the art or presently disclosed. The reference or modified suppression elements or recombinant DNA constructs can be transcribed in any plant cell or tissue or in a whole plant of any developmental stage. Transgenic plants can be derived from any monocot or dicot plant, such as, but not limited to, plants of commercial or agricultural interest, such as crop plants (especially crop plants used for human food or animal feed), wood- or pulp-producing trees, vegetable plants, fruit plants, and ornamental plants. Non-limiting examples of plants include grain crop plants (such as wheat, oat, barley, maize, rye, triticale, rice, millet, sorghum, quinoa, amaranth, and buckwheat); forage crop plants (such as forage grasses and forage dicots including alfalfa, vetch, clover, and the like); oilseed crop plants (such as cotton, safflower, sunflower, soybean, canola, rapeseed, flax, peanuts, and oil palm); tree nuts (such as walnut, cashew, hazelnut, pecan, almond, and the like); sugarcane, coconut, date palm, olive, sugarbeet, tea, and coffee; wood- or pulp-producing trees; vegetable crop plants such as legumes (for example, beans, peas, lentils, alfalfa, peanut), lettuce, asparagus, artichoke, celery, carrot, radish, the brassicas (for example, cabbages, kales, mustards, and other leafy brassicas, broccoli, cauliflower, Brussels sprouts, turnip, kohlrabi), edible cucurbits (for example, cucumbers, melons, summer squashes, winter squashes), edible alliums (for example, onions, garlic, leeks, shallots, chives), edible members of the Solanaceae (for example, tomatoes, eggplants, potatoes, peppers, groundcherries), and edible members of the Chenopodiaceae (for example, beet, chard, spinach, quinoa, amaranth); fruit crop plants such as apple, pear, citrus fruits (for example, orange, lime, lemon, grapefruit, and others), stone fruits (for example, apricot, peach, plum, nectarine), banana, pineapple, grape, kiwifruit, papaya, avocado, and berries; and ornamental plants including ornamental flowering plants, ornamental trees and shrubs, ornamental groundcovers, and ornamental grasses. Preferred dicot plants include, but are not limited to, canola, cotton, potato, quinoa, amaranth, buckwheat, safflower, soybean, sugarbeet, and sunflower, more preferably soybean, canola, and cotton. Preferred monocots include, but are not limited to, wheat, oat, barley, maize, rye, triticale, rice, ornamental and forage grasses, sorghum, millet, and sugarcane, more preferably maize, wheat, and rice.

The ultimate goal in plant transformation is to produce plants which are useful to man. In this respect, transgenic plants of the invention can be used for virtually any purpose deemed of value to the grower or to the consumer. For example, one may wish to harvest the transgenic plant itself, or harvest transgenic seed of the transgenic plant for planting purposes, or products can be made from the transgenic plant or its seed such as oil, starch, ethanol or other fermentation products, animal feed or human food, pharmaceuticals, and various industrial and commodity products. For example, maize is used extensively in the food and feed industries, as well as in industrial applications. Further discussion of the uses of maize can be found, for example, in U.S. Pat. Nos. 6,194,636, 6,207,879, 6,232,526, 6,426,446, 6,429,357, 6,433,252, 6,437,217, and 6,583,338 and PCT Publications WO 95/06128 and WO 02/057471.

Thus, in preferred embodiments, the suppression element is transcribed in a transgenic plant cell contained in a transgenic plant or plant tissue, resulting in at least one altered trait, relative to a plant or plant tissue lacking the suppression element, selected from the group of traits consisting of:
 (a) improved abiotic stress tolerance;
 (b) improved biotic stress tolerance;
 (c) improved resistance to a pest or pathogen of the plant;
 (d) modified primary metabolite composition;
 (e) modified secondary metabolite composition;
 (f) modified trace element, carotenoid, or vitamin composition;
 (g) improved yield;
 (h) improved ability to use nitrogen or other nutrients;
 (i) modified agronomic characteristics;
 (j) modified growth or reproductive characteristics; and
 (k) improved harvest, storage, or processing quality.

In particularly preferred embodiments, the transgenic plant cell, plant tissue, or plant is characterized by: improved tolerance of abiotic stress (e. g., tolerance of water deficit or drought, heat, cold, non-optimal nutrient or salt levels, non-optimal light levels) or of biotic stress (e. g., crowding, allelopathy, or wounding); by improved resistance to a pest or pathogen (e. g., insect, nematode, fungal, bacterial, or viral pest or pathogen) of the plant; by a modified primary metabolite (e. g., fatty acid, oil, amino acid, protein, sugar, or carbohydrate) composition; a modified secondary metabolite (e. g., alkaloids, terpenoids, polyketides, non-ribosomal peptides, and secondary metabolites of mixed biosynthetic origin) composition; a modified trace element (e. g., iron, zinc), carotenoid (e. g., beta-carotene, lycopene, lutein, zeaxanthin, or other carotenoids and xanthophylls), or vitamin (e. g., tocopherols) composition; improved yield (e. g., improved yield under non-stress conditions or improved yield under biotic or abiotic stress); improved ability to use nitrogen or other nutrients; modified agronomic characteristics (e. g., delayed ripening; delayed senescence; earlier or later maturity; improved shade tolerance; improved resistance to root or stalk lodging; improved resistance to "green snap" of stems; modified photoperiod response); modified growth or reproductive characteristics (e. g., intentional dwarfing; intentional male sterility, useful, e. g., in improved hybridization procedures; improved vegetative growth rate; improved germination; improved male or female fertility); improved harvest, storage, or processing quality (e. g., improved resistance to pests during storage, improved resistance to breakage, improved appeal to consumers); or any combination of these traits.

In one preferred embodiment, transgenic seed, or seed produced by the transgenic plant, has modified primary metabolite (e. g., fatty acid, oil, amino acid, protein, sugar, or carbohydrate) composition, a modified secondary metabolite (e. g., alkaloids, terpenoids, polyketides, non-ribosomal peptides, and secondary metabolites of mixed biosynthetic origin) composition, a modified trace element (e. g., iron, zinc), carotenoid (e. g., beta-carotene, lycopene, lutein, zeaxanthin, or other carotenoids and xanthophylls), or vitamin (e. g., tocopherols,) composition, an improved harvest, storage, or processing quality, or a combination of these. For example, it can be desirable to modify the amino acid (e. g., lysine, methionine, tryptophan, or total protein), oil (e. g., fatty acid composition or total oil), carbohydrate (e. g., simple sugars or starches), trace element, carotenoid, or vitamin content of seeds of crop plants (e. g., canola, cotton, safflower, soybean, sugarbeet, sunflower, wheat, maize, or rice), preferably in combination with improved seed harvest, storage, or processing quality, and thus provide improved seed for use in animal feeds or human foods. In another instance, it can be desirable to change levels of native components of the transgenic plant or seed of a transgenic plant, for example, to decrease levels of proteins with low levels of lysine, methionine, or tryptophan, or to increase the levels of a desired amino acid or fatty acid, or to decrease levels of an allergenic protein or glycoprotein (e. g., peanut allergens including ara h 1, wheat allergens including gliadins and glutenins, soy allergens including P34 allergen, globulins, glycinins, and conglycinins) or of a toxic metabolite (e. g., cyanogenic glycosides in cassava, solanum alkaloids in members of the Solanaceae).

EXAMPLES

Example 1

This example illustrates a non-limiting example of a method of modifying the degree of silencing of a target gene, including transcribing in a eukaryotic cell a, thereby obtaining a modified degree of silencing of the target gene, relative to a modified suppression element reference degree of silencing obtained through the transcription in the eukaryotic cell of a reference suppression element that corresponds to the target gene. More particularly, this example describes a method including selection of a modified suppression element by mapping silencing efficacy.

Mapping the silencing efficacy of suppression elements for the target gene can be carried out, for example, by empirically determining the silencing efficacy of each of a plurality of fragments of a given reference suppression element that corresponds to the target gene. One embodiment of the method includes "scanning" the reference suppression element, that is, determining the silencing efficacy of fragments of the reference suppression element. The first fragments can be contiguous or non-contiguous, and can overlap. Generally, each of the first fragments includes from about 1% to about 98% of the reference suppression element; however, the reference suppression element may be divided into as many first fragments as is convenient or desirable. One non-limiting example of scanning includes the steps of: (a) providing a reference suppression element corresponding to the target gene, wherein transcription of the reference suppression element in a eukaryotic cell results in a reference degree of silencing of the target gene; (b) providing a plurality of first fragments of the reference suppression element; and (c) empirically determining the degree of silencing of the target gene for each of the first fragments when transcribed in the eukaryotic cell; and (d) selecting at least one first fragment that provides a desired degree of silencing of the target gene for use in a modified suppression element.

Another non-limiting example of scanning includes the steps of: (a) providing a reference suppression element corresponding to the target gene, wherein transcription of the reference suppression element in a eukaryotic cell results in a reference degree of silencing of the target gene; (b) providing a plurality of first fragments of the reference suppression element; (c) empirically determining the degree of silencing of the target gene for each of the first fragments when transcribed in the eukaryotic cell; (d) selecting at least one first fragment that provides a desired degree of silencing of the target gene for use in a modified suppression element; (e) for the selected at least one first fragment, providing a plurality of second fragments each consisting of nucleotide segments of the first fragment; empirically determining the degree of silencing of the target gene for each of the second fragments when transcribed in the eukaryotic cell; and (f) selecting at least one second fragment that provides a desired degree of silencing of the target gene for use in a modified suppression element. The fragments can be contiguous or non-contiguous, and can overlap. The second fragments consist of from about one nucleotide shorter than the at least one first fragment to about 21 nucleotides in length. Fragments thus derived can be combined, e. g., as multiple copies of one or more fragments in chimeric combinations, or in combination with other suppression elements or expression elements.

The method of the invention is further illustrated by the following example, which describes mapping silencing efficacy of suppression elements for the target gene corn rootworm V-ATPase subunit A by analysis of fragments of a reference suppression element (FIG. 1). A bioassay for larval mortality served as a proxy measurement of target gene silencing efficacy. The reference suppression element, a 600 nucleotide segment of Western corn rootworm ("WCR", *Diabrotica virgifera*) V-ATPase subunit A was found to induce a reference degree of silencing of ~79% mortality when fed as double-stranded RNA (0.02 ppm) to WCR larvae. Four contiguous ~150 nucleotide fragments of this ~600 nucleotide V-ATPase segment were separately synthesized and fed as dsRNA (0.02 ppm) to WCR larvae; these modified suppression elements were found to induce modified degrees of suppression of 18%, 75%, 50%, and 12% mortality, respectively (FIG. 1). Thus, the modified degree of suppression resulting from transcription in a eukaryotic cell (e. g., in a transgenic corn plant cell developed for resistance to corn rootworm) of these ~150 nucleotide modified suppression elements is decreased suppression (e. g., decreased WCR larval mortality), relative to the suppression observed for the reference suppression element.

Another suppression element, consisting of a 100 nucleotide subfragment of the ~150 nucleotide fragment that induced 75% mortality at 0.02 ppm (FIG. 1), was selected for further efficacy mapping. The 100 base pair fragment was amplified by PCR with the appropriate primers to produce an antisense template and a sense template. The sense and antisense reactions were mixed, heated to 75 degrees Celsius for 5 minutes and allowed to cool to room temperature. The resulting annealed 100 base pair double-stranded RNA product was purified with the MEGAscript™ RNAi Kit (Ambion, Cat #1626) according to the manufacturer's instructions to produce a 100 base pair dsRNA product which was then tested with the same WCR larval bioassay. When fed to WCR larvae at 0.2 ppm, the 100 bp dsRNA suppression element induced 100% mortality (FIG. 1). A control (double-stranded RNA derived from 108 base pairs of vector sequence) caused no mortality at the same feeding concentration.

The 100 bp suppression element was further mapped at a resolution of 26 bp fragments in a 5 bp register (FIG. 1). Fifteen 26 bp segments (designated scans 0 to 14) derived from the 100 bp suppression element were produced synthetically (Integrated DNA Technologies) as sense and antisense oligonucleotides. Each pair of sense and antisense oligonucleotides was annealed, and a 3' overhang was added by PCR with REDtaq polymerase. The fifteen cloned 26 bp segments were verified for correct sequence and orientation, and used as PCR templates. PCR reaction products were checked on agarose gels for correct size and quality, and amplified for dsRNA synthesis using MEGAscript RNAi Kit (Ambion, Cat #1626). Final dsRNA products were quantified by absorption at 260 nanometers, and visualized on a 1-3% agarose gel to ensure intactness of the product.

Double-stranded RNA corresponding to the fifteen 26 bp fragments (Scan 0 to Scan 14, see Table 1 and FIG. 1) was amplified in a larger neutral carrier (vector backbone sequence), and dsRNA was synthesized for a total assayed dsRNA length of 206 bp. All samples for insect bioassay were diluted to the final desired concentration in 10 millimolar Tris pH 6.8. Twenty microliters of each sample were applied to 200 microliters of insect diet and allowed to absorb into the diet before addition of a WCR neonate. Stunting and mortality of larvae was scored at day 12. When fed at 1 ppm, the dsRNAs synthesized from the 26 bp fragments resulted in a range of mortality from no significant difference from the untreated control to approximately 95% mortality (Scan 7 fragment). A lower dose of 0.2 ppm was useful in identifying the most active segments, with observed mortality ranging from no significant difference from the untreated control (Scan 10 fragment) to 97% mortality (Scan 3 fragment) (Table 1 and FIG. 1).

TABLE 1

26mer mapping

| dsRNA | Larval mortality[1] in WCR diet bioassay at 1 ppm | Larval mortality[1] in WCR diet bioassay at 0.2 ppm |
|---|---|---|
| Scan 0 | 60.1 ± 4.4* | 13.3 ± 9.7 |
| Scan 1 | 36.4 ± 16.3* | 16.3 ± 4.3 |
| Scan 2 | 35.8 ± 9.1* | 22.6 ± 3.3* |
| Scan 3 | 85.7 ± 9.0* | 96.7 ± 3.30* |
| Scan 4 | 75.0 ± 9.4* | 42.8 ± 3.8* |
| Scan 5 | 65.4 ± 11.4* | 39.4 ± 10.7* |
| Scan 6 | 92.5 ± 5.0* | 61.9 ± 8.5* |
| Scan 7 | 94.6 ± 3.3* | 80.6 ± 9.4* |
| Scan 8 | 91.0 ± 5.61* | 66.7 ± 10.0* |
| Scan 9 | 41.4 ± 6.8* | 19.0 ± 7.5 |
| Scan 10 | 7.9 ± 5.1 | 6.7 ± 4.1 |
| Scan 11 | 39.3 ± 5.3* | 5.4 ± 3.3 |
| Scan 12 | 37.9 ± 6.9* | 13.7 ± 6.9 |

TABLE 1-continued

26mer mapping

| dsRNA | Larval mortality[1] in WCR diet bioassay at 1 ppm | Larval mortality[1] in WCR diet bioassay at 0.2 ppm |
|---|---|---|
| Scan 13 | 61.2 ± 6.3* | 33.3 ± 12.6* |
| Scan 14 | 70.6 ± 7.3* | 42.3 ± 7.8* |
| 100 bp suppression element | 100* | 100* |
| Control, vector sequence only | NA | 0.0* |

[1]Percent mortality and standard error of the means.
*significantly different from untreated control, P value <0.05, Planned Contrasts.
NA = not assayed Scan 14 (26 bp) was further mapped into its seven possible 21 bp fragments (designated scans 15-21) (Table 2 and FIG. 1). Attempts were made to clone all seven possible 21mers, but cloning of scan 15 failed and the cloned scan 17 sequence was found to contain a point mutation. Nonetheless, the successfully cloned 21mers were amplified to produce templates, and embedded in neutral (vector) carrier sequence to give a final dsRNA size of 184 bp. Samples were diluted, applied at 0.2 ppm, and assayed with the WCR larval diet bioassay as previously done. Most were found to possess significant activity (Table 2). Of particular interest is the unpredicted discrepancy between the observed silencing efficacy (indicated by larval mortality) and the Reynolds scores of the tested fragments. A higher positive Reynolds score (Reynolds et al. 2004) has been believed to be predictive a greater probability of gene suppression. Unexpectedly, the fragment with the highest Reynolds score (Scan 21, Table 2) gave the lowest activity, and the fragment with the lowest Reynolds score (Scan 16, Table 2), provided the highest activity of the tested 21mers. These observed discrepancies emphasize the need for empirical testing in mapping efficacy of suppression elements.

TABLE 2

21mer mapping

| dsRNA | Reynolds score (for 21mer) | Larval mortality[1] in WCR diet bioassay at 1 ppm | Larval mortality[1] in WCR diet bioassay at 0.2 ppm |
|---|---|---|---|
| Scan 14 (see Table 1) | not applicable | 92.0 ± 8.0* | 77.3 ± 7.6* |
| Scan 15 | 3 | NA | NA |
| Scan 16 | 1 | 92.1 ± 5.1* | 53.2 ± 7.9* |
| Scan 17 | 3 | 13.6 ± 6.0 | 0.0 |
| Scan 18 | 4 | 77.8 ± 10.0* | 43.2 ± 9.2* |
| Scan 19 | 6 | 73.3 ± 7.3* | 76.1 ± 9.6* |
| Scan 20 | 8 | 85.3 ± 6.2* | 77.1 ± 7.1* |
| Scan 21 | 9 | 5.0 ± 5.0 | 0.0 |
| 100 bp suppression element | not applicable | 97.1 ± 2.9* | NA |
| Control, vector sequence only | not applicable | 0.0 | NA |

[1]Percent mortality and standard error of the means.
*significantly different from untreated control, P value <0.05, Planned Contrasts.
NA = not assayed Example 2

This example illustrates a non-limiting example of modifying the degree of silencing of a target gene, including transcribing in a eukaryotic cell a modified suppression element, thereby obtaining a modified degree of silencing of the target gene, relative to a reference degree of silencing obtained through the transcription in the eukaryotic cell of a reference suppression element that corresponds to the target gene. More particularly, this example describes a modified suppression element provided by truncation of a reference suppression element and a modified degree of silencing as evidenced by a modified phenotype in a seed containing the eukaryotic cell.

Furthermore, this example illustrates a method of providing a eukaryotic cell having a desired phenotype resulting from transcription in the eukaryotic cell of a modified suppression element. In one embodiment, the method includes the steps of: (a) providing a range of modified suppression elements, wherein each modified suppression element includes a fragment of a reference suppression element; (b) separately introducing each of the modified suppression elements into a eukaryotic cell, thereby producing a plurality of transgenic eukaryotic cells (c) transcribing in each of the transgenic eukaryotic cells the modified suppression element therein introduced, and observing the resulting phenotype resulting from the transcribing; and (d) selecting from the plurality of transgenic eukaryotic cells at least one eukaryotic cell having the desired phenotype. In this non-limiting example, the eukaryotic cell is a plant cell, specifically a transgenic crop plant cell, the target gene includes non-coding sequence, the modified suppression elements are a series of truncations of a reference suppression element, and the desired phenotype is observed in a seed including the transgenic crop plant cell.

The target gene in this example is non-coding sequence, an intron of a soybean (*Glycine max*) fatty acid desaturase FAD2 or delta-12 desaturase gene, which encodes an enzyme that catalyzes the insertion of a double bond into a monounsaturated 18:1 fatty acid to form a polyunsaturated 18:2 fatty acid. Suppression of FAD2 results in an increase of 18:1 fatty acid content in the seed.

Figure 2:
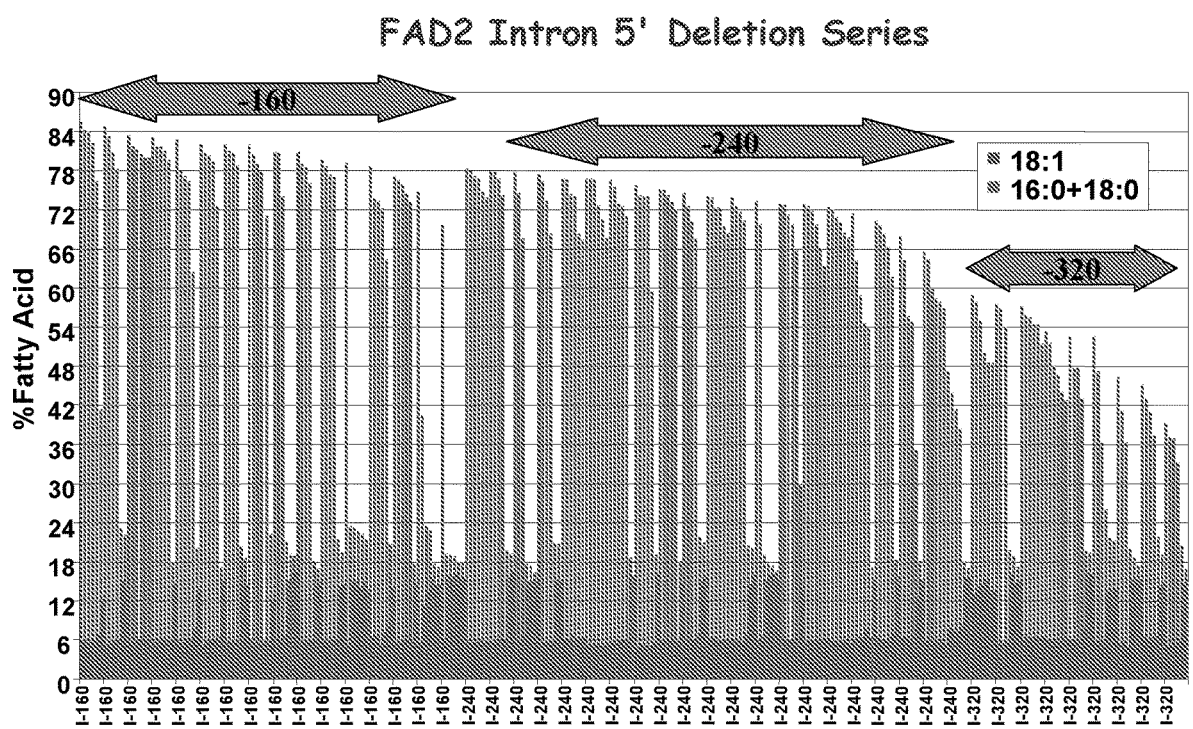
FIG. 2 depicts results of the experiments described in Example 2 as a plot of 18:1 fatty acid levels as a function of size of the suppression element.

To obtain a desired level of 18:1 fatty acids, the degree of silencing of the target gene was modified by use of modified suppression elements. Examples of recombinant DNA constructs, including constructs containing suppression elements targetting FAD2 sequences, and detailed descriptions of their use, as well as of methods to make and use transgenic soybean seed, are provided in United States Patent Application Publication 2004/0107460, which is incorporated by reference in its entirety herein. A reference suppression element including sequence that transcribed to double-stranded RNA corresponding to the FAD2 intron was introduced into soybean by *Agrobacterium*-mediated stable transformation, resulting in increased 18:1 fatty acid content. A range of modified suppression elements was designed, wherein each modified suppression element was derived by truncation of the reference suppression element to correspond respectively to a deletion of ~160, ~240, or ~320 nucleotides from the 5' end of the target gene (FAD2 intron). Each modified suppression element was introduced into soybean cells by *Agrobacterium*-mediated stable transformation, and stably transformed soybean plants generated. FIG. 2 depicts the results of transcribing the modified suppression element in soybean, where, on average, the degree of FAD2 silencing (observed as increased 18:1 fatty acid levels) was modulated or decreased in comparison to that obtained with the reference suppression element. Fatty acid content of individual seeds (six seeds per transformation event, with each event indicated on the x-axis of FIG. 2) was analyzed by gas chromatography. Silencing of the target gene FAD2 (evidenced by increased 18:1 fatty acid content) was modified or decreased, with modulation (decrease in suppression) generally proportional to the degree of truncation (deletion of sequence from the reference suppression element) used in a given modified suppression element, e. g., the increase in average 18:1 fatty acid content was less in seeds transformed with the 320-nucleotide truncated modified suppression element than in seeds transformed with the 240-nucleotide truncated modified suppression element. Seed having the desired phenotype (i. e., a given 18:1 fatty acid content) could then be selected from the range of phenotypes presented.

Figure 3:
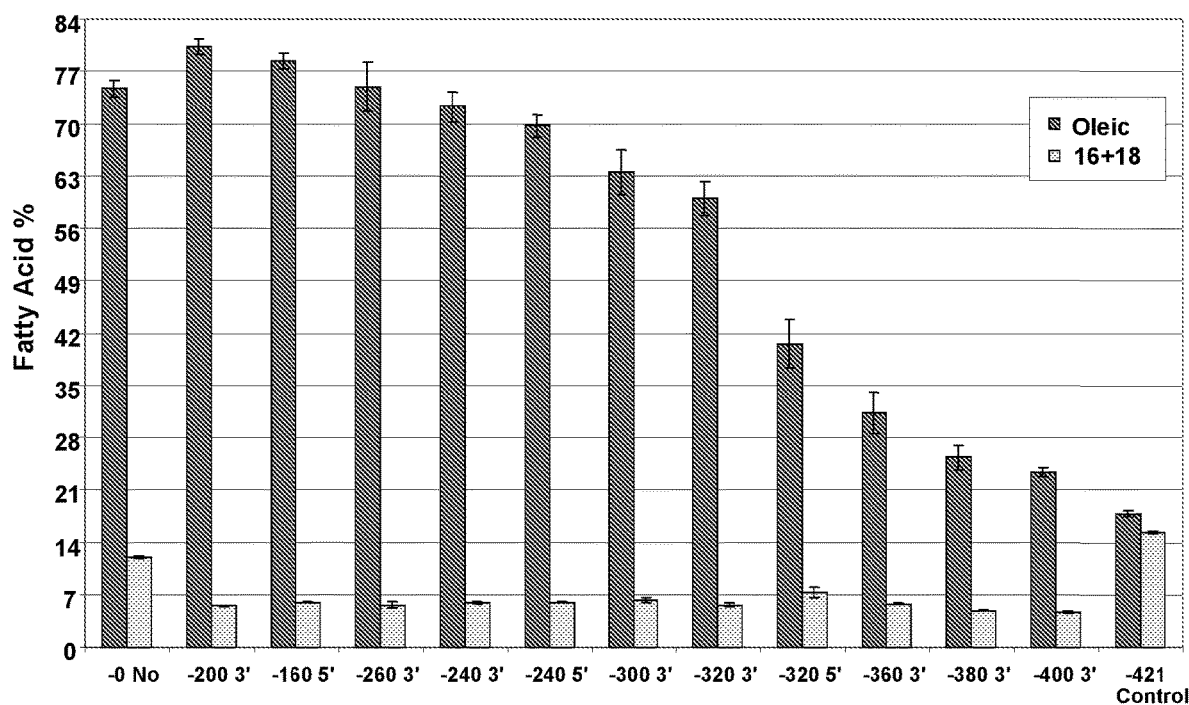
FIG. 3 depicts results of the experiments described in Example 2, as a plot of 18:1 fatty acid levels as a function of size of the suppression element.

A separate experiment (FIG. 3) was carried out with modified suppression elements wherein each modified suppression element was derived by truncation of the reference suppression element to correspond respectively to a deletion of ~160, ~240, or ~320 nucleotides from the 5' end of the target gene (FAD2 intron) or to a deletion of ~200, ~240, ~260, ~300, ~320, ~360, ~380, ~400 nucleotides from the 3' end of the target gene (FAD2 intron). A suppression element corresponding to complete deletion (421 nucleotides) of the target gene (FAD2 intron) served as a control. Various, modified degrees of silencing of FAD2 (evidenced by increased 18:1 fatty acid content) were obtained in the different transgenic events, when compared to that obtained with the unmodified reference suppression element ("0 No"). Seed having the desired phenotype (i. e., a given 18:1 fatty acid content) could then be selected from the range of phenotypes presented.

All of the materials and methods disclosed and claimed herein can be made and used without undue experimentation as instructed by the above disclosure. Although the materials and methods of this invention have been described in terms of preferred embodiments and illustrative examples, it will be apparent to those of skill in the art that variations can be applied to the materials and methods described herein without departing from the concept, spirit and scope of the invention. All such similar substitutes and modifications apparent to those skilled in the art are deemed to be within the spirit, scope and concept of the invention as defined by the appended claims.

What is claimed is:

1. A method for providing a modified soybean seed with a desired phenotype, wherein the desired phenotype is an oleic acid content of about 40% to about 85% by weight of the total fatty acids and a saturated fatty acid content of less than 8% by weight of the total fatty acids, comprising:
    (a) providing a range of modified suppression elements, wherein each modified suppression element comprises a DNA fragment of a fatty acid desaturase 2 (FAD2) intron,
    wherein the range comprises at least three modified suppression elements, each comprising a different length DNA fragment of a FAD2 intron, wherein the lengths are from 19 contiguous base pairs of a FAD2 intron to 400 contiguous base pairs of a FAD2 intron,
    wherein the DNA fragment comprises at least one anti-sense segment that is anti-sense to at least one segment of a FAD2 intron, and at least one sense segment that is at least one segment of a FAD2 intron;
    (b) separately introducing each modified suppression element into a soybean cell, thereby producing a plurality of modified soybean cells;
    (c) obtaining a population of modified soybean seeds comprising the modified soybean cells;
    (d) transcribing to RNA in each of the modified soybean seeds the modified suppression element therein introduced, wherein the RNA suppresses FAD2 by forming a double-stranded RNA, wherein the amount of FAD2 suppression in each modified soybean seed depends on the length of the FAD2 intron fragment in the modified soybean seed, and decreases in FAD2 intron fragment length decrease the suppression of FAD2 in a modified soybean seed, and observing the phenotype resulting from the transcribing, wherein the phenotype is the percentage oleic acid content by weight of the total fatty acids and the percentage saturated fatty acid content by weight of the total fatty acids of the seed; and
    (e) selecting from the population of modified soybean seeds at least one soybean seed comprising the modified soybean cells, wherein the modified soybean seed has the desired phenotype.

2. A method for providing modified soybean seeds with a desired phenotype, wherein the desired phenotype is an average oleic acid content of about 40% to about 85% by weight of the total fatty acids and an average saturated fatty acid content of less than 8% by weight of the total fatty acids, comprising:
    (a) providing a range of modified suppression elements, wherein each modified suppression element comprises a DNA fragment of a fatty acid desaturase 2 (FAD2) intron,
    wherein the range comprises at least three modified suppression elements, each comprising a different length DNA fragment of a FAD2 intron, wherein the lengths are from 19 contiguous base pairs of a FAD2 intron to 400 contiguous base pairs of a FAD2 intron,
    wherein the DNA fragment comprises at least one anti-sense segment that is anti-sense to at least one segment of a FAD2 intron, and at least one sense segment that is at least one segment of a FAD2 intron;
    (b) separately introducing each modified suppression element into a soybean cell, thereby producing a plurality of modified soybean cells;
    (c) obtaining a first population of modified soybean seeds comprising the modified soybean cells;
    (d) transcribing to RNA in each of the modified soybean seeds the modified suppression element therein introduced, wherein the RNA suppresses FAD2 by forming a double-stranded RNA, wherein the amount of FAD2 suppression in each modified soybean seed depends on the length of the FAD2 intron fragment in the modified soybean seed, and decreases in FAD2 intron fragment length decrease the suppression of FAD2 in a modified soybean seed, and observing the phenotype resulting from the transcribing, wherein the phenotype is the percentage oleic acid content by weight of the total fatty acids and the percentage saturated fatty acid content by weight of the total fatty acids of the seed; and
    (e) selecting from the first population of modified soybean seeds a second population of soybean seeds comprising the modified soybean cells, wherein the second population of modified soybean seeds has wing the desired phenotype.

3. The method of claim 1, wherein the DNA fragment in at least one modified soybean seed comprises a truncation of the FAD2 intron corresponding to a deletion of nucleotides from the 5' end of the at least one sense segment and the complementary nucleotides of the anti-sense segment.

4. The method of claim 2, wherein the DNA fragment in at least one modified soybean seed comprises a truncation of the FAD2 intron corresponding to a deletion of nucleotides from the 5' end of the at least one sense segment and the complementary nucleotides of the anti-sense segment.

5. The method of claim 1, wherein the DNA fragment in at least one modified soybean seed comprises a truncation of the FAD2 intron corresponding to a deletion of nucleotides from the 3' end of the at least one sense segment and the complementary nucleotides of the anti-sense segment.

6. The method of claim 2, wherein the DNA fragment in at least one modified soybean seed comprises a truncation of the FAD2 intron corresponding to a deletion of nucleotides from the 3' end of the at least one sense segment and the complementary nucleotides of the anti-sense segment.

7. The method of claim 1, wherein the providing a range of modified suppression elements comprises the use of *Agrobacterium*-mediated transformation.

8. The method of claim 1, wherein the providing a range of modified suppression elements comprises the use of microprojectile bombardment.

9. The method of claim 1, wherein the providing a range of modified suppression elements comprises the use of PEG-mediated transformation of soybean protoplasts.

10. The method of claim 1, wherein the method further comprises (f) generating a soybean plant from the at least one soybean seed comprising the modified soybean cells having the desired phenotype.

11. The method of claim 10, wherein the method further comprises (g) crossing the at least one soybean plant with a second soybean plant.

12. The method of claim 10, wherein the method further comprises (g) self-pollinating the at least one soybean plant.

13. The method of claim 2, wherein the providing a range of modified suppression elements comprises the use of *Agrobacterium*-mediated transformation.

14. The method of claim 2, wherein the providing a range of modified suppression elements comprises the use of microprojectile bombardment.

15. The method of claim 2, wherein the providing a range of modified suppression elements comprises the use of PEG-mediated transformation of soybean protoplasts.

16. The method of claim 2, wherein the method further comprises (f) generating a soybean plant from at least one soybean seed from the second population of soybean seeds comprising the modified soybean cells, wherein the second population of modified soybean seeds has the desired phenotype.

17. The method of claim 16, wherein the method further comprises (g) crossing the at least one soybean plant with a second soybean plant.

18. The method of claim 16, wherein the method further comprises (g) self-pollinating the at least one soybean plant.

* * * * *